US011680392B2

(12) United States Patent
Kramer et al.

(10) Patent No.: US 11,680,392 B2
(45) Date of Patent: Jun. 20, 2023

(54) DRINKING WATER SUPPLY SYSTEM WITH GROUPWISE CONTROL, METHOD FOR CONTROLLING THE SAME, AND COMPUTER PROGRAM

(71) Applicant: Viega Technology GmbH & Co. KG, Attendorn (DE)

(72) Inventors: Markus Kramer, Eslohe (DE); Christian Schauer, Arnsberg (DE); Christian Otto, Heiligenhaus (DE); Patrick Steger, Kreuztal (DE); David Löher, Lennestadt (DE); Arthur Winterholler, Attendorn (DE)

(73) Assignee: Viega Technology GmbH & Co. KG, Attendorn (DE)

( * ) Notice: Subject to any disclaimer, the term of this patent is extended or adjusted under 35 U.S.C. 154(b) by 0 days.

(21) Appl. No.: 16/753,835

(22) PCT Filed: Oct. 9, 2018

(86) PCT No.: PCT/EP2018/077410
§ 371 (c)(1),
(2) Date: Apr. 6, 2020

(87) PCT Pub. No.: WO2019/072807
PCT Pub. Date: Apr. 18, 2019

(65) Prior Publication Data
US 2020/0284006 A1  Sep. 10, 2020

(30) Foreign Application Priority Data

Oct. 9, 2017 (DE) ..................... 10 2017 123 437.3
Apr. 13, 2018 (DE) ..................... 10 2018 108 850.7

(51) Int. Cl.
*E03C 1/05* (2006.01)
*E03B 7/02* (2006.01)
(Continued)

(52) U.S. Cl.
CPC .............. *E03B 7/075* (2013.01); *E03B 7/006* (2013.01); *E03B 7/02* (2013.01); *E03B 7/04* (2013.01);
(Continued)

(58) Field of Classification Search
CPC ..... E03B 7/02; E03B 7/04; E03B 7/08; E03B 7/075; E03B 7/006; E03B 7/045;
(Continued)

(56) References Cited

U.S. PATENT DOCUMENTS 5,438,714 A   8/1995 Shaw
6,000,429 A  12/1999 Van Marcke
(Continued)

FOREIGN PATENT DOCUMENTS

CA        2363744 A1   5/2003
CN        1421577 A    6/2003
(Continued)

OTHER PUBLICATIONS

"ESchell vernetzt x mal 64 Sanitararmaturen über Funk und oder Kabel" (eSchell connects x times 64 sanitary fittings via radio and/or cable), https://www.baulinks.de/webplugin/2016/0582.php4 (May 3, 2016).
(Continued)

*Primary Examiner* — Akash K Varma
(74) *Attorney, Agent, or Firm* — The Webb Law Firm

(57) ABSTRACT

The invention relates to a drinking water supply system including a drinking water line system, a plurality of drinking water withdrawal points connected to the drinking water line system, at least one sensor which is designed to determine measuring values, a central control device which is designed to receive and evaluate the measuring values determined by the at least one sensor, a plurality of decentralized control elements which are designed to influence at
(Continued)

different locations in the drinking water supply system one or more properties of the water guided in the drinking water supply system, wherein the central control device is designed to control the control elements for influencing the one or more properties of the water guided in the drinking water supply system, and wherein a plurality of control elements are or can be combined to form a virtual group.

13 Claims, 13 Drawing Sheets

(51) Int. Cl.
    *E03B 7/04*     (2006.01)
    *E03D 5/10*     (2006.01)
    *E03B 7/07*     (2006.01)
    *E03B 7/00*     (2006.01)
    *E03B 7/08*     (2006.01)
    *G01N 33/18*     (2006.01)
    *E03C 1/02*     (2006.01)

(52) U.S. Cl.
    CPC ............... *E03B 7/045* (2013.01); *E03B 7/07* (2013.01); *E03B 7/072* (2013.01); *E03B 7/074* (2013.01); *E03B 7/08* (2013.01); *E03C 1/02* (2013.01); *E03C 1/055* (2013.01); *E03D 5/105* (2013.01); *G01N 33/1826* (2013.01); *G01N 33/1853* (2013.01); *E03B 7/078* (2013.01)

(58) Field of Classification Search
    CPC . E03B 7/07; E03B 7/072; E03B 7/074; E03B 7/078; E03B 7/00; E03C 1/02; E03C 1/055; E03C 1/05; E03D 5/105; E03D 5/10; G01N 33/1826; G01N 33/1853; G01N 33/18; B42D 25/23; B42D 25/29; B42D 25/328; B42D 25/355; B42D 25/364; G02B 5/0252; G02B 5/0257; G03H 1/0011; G03H 1/0244; G07D 7/0032
    USPC .......................................................... 700/284
    See application file for complete search history.

(56) References Cited

U.S. PATENT DOCUMENTS

| | | | |
|---|---|---|---|
| 7,304,569 | B2 | 12/2007 | Marcichow |
| 8,310,369 | B1 | 11/2012 | Canfield et al. |
| 8,364,546 | B2 | 1/2013 | Yenni et al. |
| 8,984,675 | B2 | 3/2015 | Miller et al. |
| 9,493,931 | B2 | 11/2016 | Burrows |
| 2005/0022871 | A1 | 2/2005 | Acker |
| 2005/0171709 | A1* | 8/2005 | Nortier .................. E03C 1/057 |
| | | | 702/45 |
| 2007/0090059 | A1* | 4/2007 | Plummer ................ C02F 1/008 |
| | | | 210/743 |
| 2008/0105305 | A1 | 5/2008 | Lum et al. |
| 2008/0109175 | A1 | 5/2008 | Michalak |
| 2008/0141447 | A1 | 6/2008 | Bowcutt et al. |
| 2008/0232302 | A1 | 9/2008 | Chiu |
| 2010/0156632 | A1* | 6/2010 | Hyland ................ G08B 25/009 |
| | | | 340/540 |
| 2011/0303311 | A1 | 12/2011 | Kilcpera |
| 2012/0211085 | A1 | 8/2012 | Abbing |
| 2013/0327410 | A1 | 12/2013 | Acker |
| 2014/0332088 | A1* | 11/2014 | Senesh ...................... E03B 1/02 |
| | | | 137/14 |
| 2017/0254052 | A1* | 9/2017 | Bartenstein ............ G01K 13/02 |
| 2018/0171607 | A1 | 6/2018 | Ramos et al. |
| 2018/0180298 | A1 | 6/2018 | Abbing |
| 2019/0330091 | A1 | 10/2019 | Hank et al. |

FOREIGN PATENT DOCUMENTS

| | | |
|---|---|---|
| CN | 202544024 U | 11/2012 |
| CN | 103663575 A | 3/2014 |
| CN | 103807482 A | 5/2014 |
| CN | 204098133 U | 1/2015 |
| CN | 105908800 A | 8/2016 |
| CN | 205679934 U | 11/2016 |
| DE | 102006039701 B3 | 10/2007 |
| DE | 202012102881 U1 | 1/2013 |
| DE | 102014208261 A1 | 11/2015 |
| DE | 202014007233 U1 | 1/2016 |
| EP | 1845207 A1 | 10/2007 |
| EP | 1898010 A2 | 3/2008 |
| EP | 2466019 A2 | 6/2012 |
| EP | 2993271 A1 | 3/2016 |
| EP | 3214230 A1 | 9/2017 |
| GB | 2502165 A | 11/2013 |
| KR | 101465775 B1 | 12/2014 |
| WO | 2011053237 A1 | 5/2011 |
| WO | 2013076721 A1 | 5/2013 |

OTHER PUBLICATIONS

Screencaptures from eSchell Waste Management HD Video, https://www.youtube.com/watch?v=snHiiJ0_CQg (May 5, 2016).
"Preisliste 2017 Auszuge" (extracts from Schell GmbH & Co. KG 2017 Pricelist), http://www.schell.eu/deutschland-de/service/infomaterial.html (Jun. 6, 2017).
"Connect sanitary fittings intelligently, with eSchell" brochure, http://www.schell.eu/uploads/txdbdownloads/SCHE_eSCHELL_inet.pdf (Jun. 25, 2017).
"Anleitung zur Inbetriebnahme und Konfiguration 01-17" (Instructions for commissioning and configuration, eSchell water management system), http://www.schell.eu/deutschland-de/service/downloads/eschell.html, (May 29, 2017).
"Bedienungsanleitung" (Operating Instructions, eSchell Water Management System) http://www.schell.eu/deutschland-de/service/downloads/eschell.html (May 29, 2017).
"Systemanleitung" (System manual, eSchell water management system) http://www.schell.eu/deutschland-de/service/downloads/eschell.html (May 29, 2017).

* cited by examiner

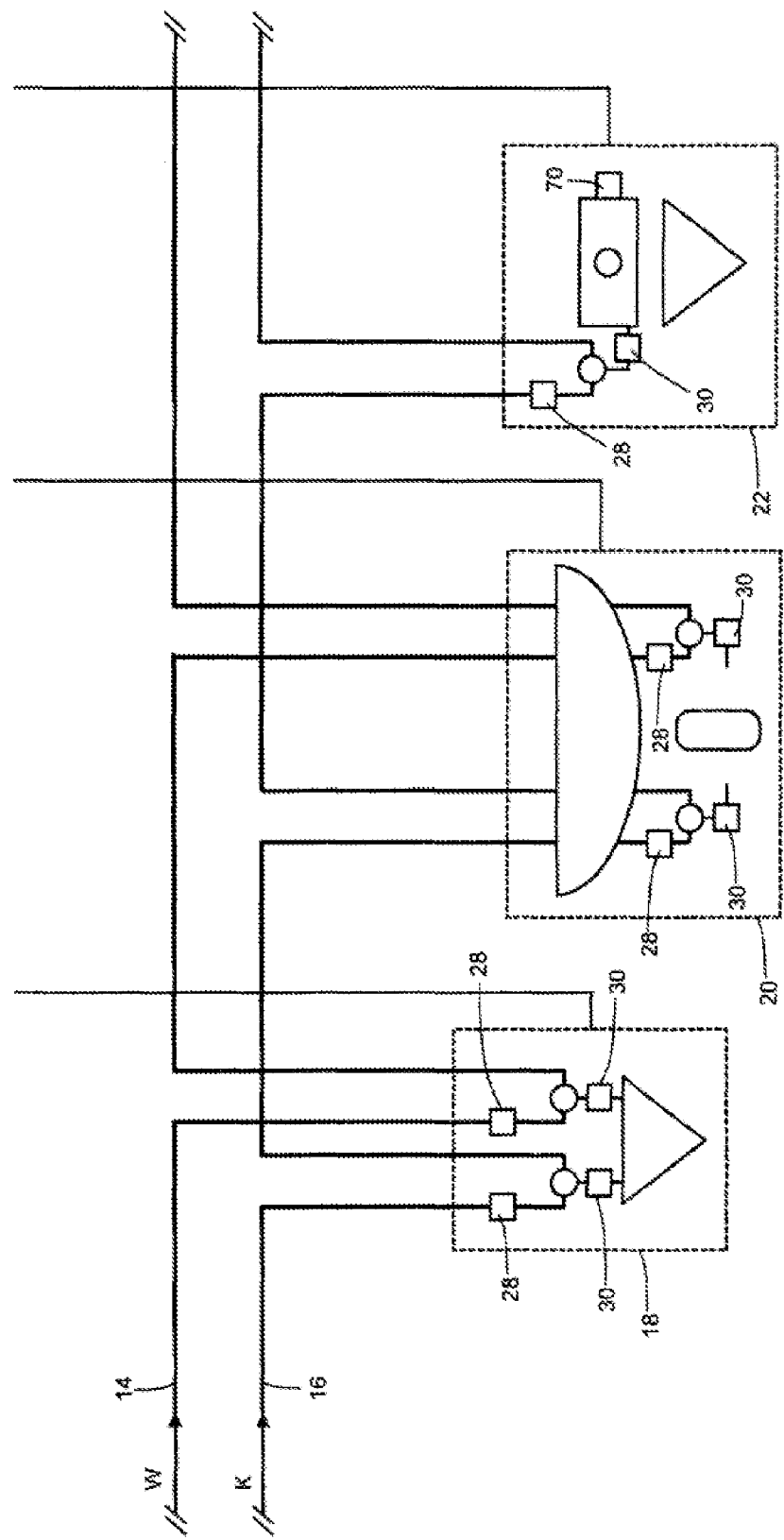

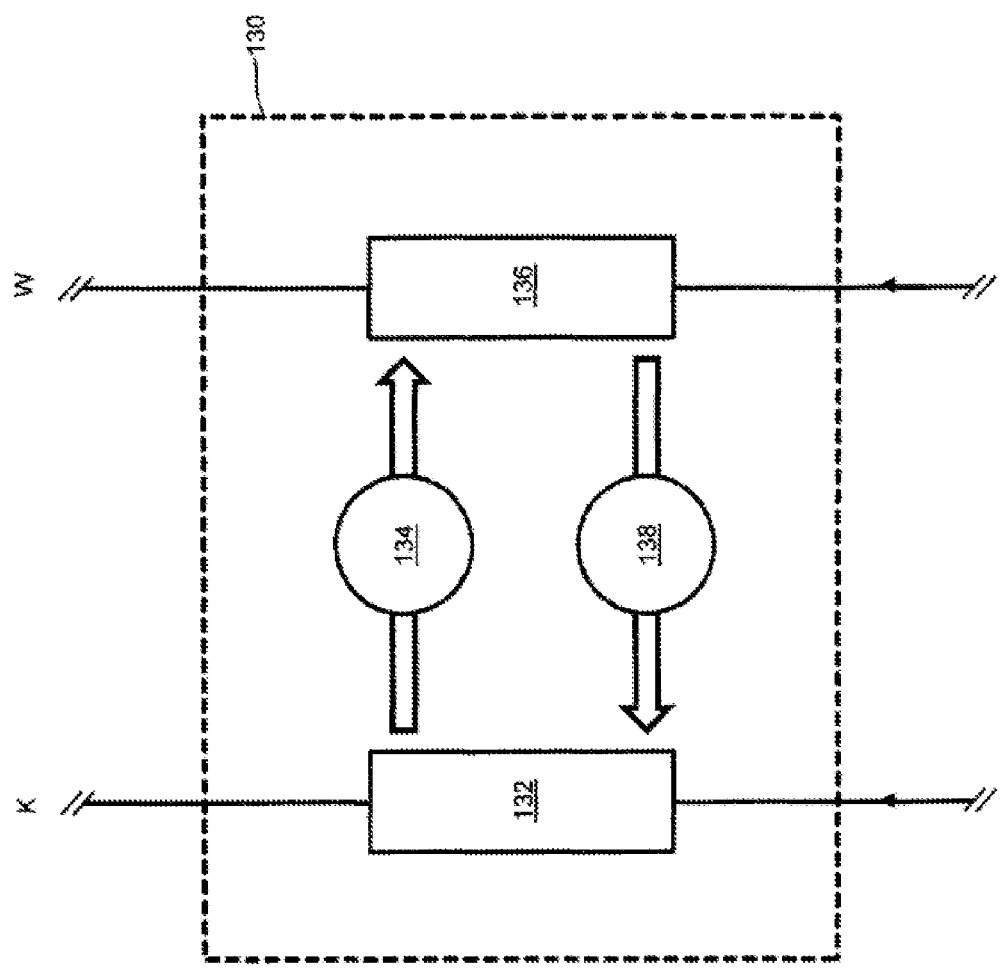

DRINKING WATER SUPPLY SYSTEM WITH GROUPWISE CONTROL, METHOD FOR CONTROLLING THE SAME, AND COMPUTER PROGRAM

CROSS-REFERENCE TO RELATED APPLICATIONS

This application is the United States national phase of International Application No. PCT/EP2018/077410, filed Oct. 9, 2018, and claims priority to German Patent Application Nos. 10 2017 123 437.3, filed Oct. 9, 2017, and 10 2018 108 850.7, filed Apr. 13, 2018, the disclosures of which are hereby incorporated by reference in their entirety.

BACKGROUND OF THE INVENTION

Field of the Invention

The invention relates to a drinking water supply system comprising a drinking water piping system and a plurality of drinking water tapping points connected to the drinking water piping system. The invention further relates to a method for controlling a drinking water supply system and to a computer program.

Description of Related Art

Drinking water supply systems of larger buildings and facilities, such as for example a hotel or a hospital, are complex systems with a branched drinking water piping system and a plurality of drinking water tapping points connected thereto. In the case of such buildings, there are also high requirements for the water quality, energy efficiency and convenience when operating the drinking water supply system.

It has been found that the complexity of the drinking water supply systems makes it difficult in such buildings to ensure the desired water quality at all times, at every drinking water tapping point and irrespective of the individual use of the drinking water supply system. Furthermore, failures of individual components of such a drinking water supply system can, under certain circumstances, go unnoticed for an extended time, whereby the local drinking water supply is disrupted or the water quality can suffer.

Against this background, the object of the present invention is to provide a drinking water supply system, a method for controlling the same, and a computer program, by means of which the drinking water supply and in particular the drinking water quality, energy efficiency and the convenience in complex drinking water supply systems can be maintained or improved.

SUMMARY OF THE INVENTION

This object is achieved according to the invention by a drinking water supply system comprising a drinking water piping system, comprising a plurality of drinking water tapping points connected to the drinking water piping system, comprising at least one sensor configured to determine measurement values and comprising a central control device configured to receive and evaluate the measurement values determined by the at least one sensor. A plurality of sensors are preferably provided which are configured to determine measurement values for one or different properties of the water carried in the drinking water supply system at different points in the drinking water supply system and the central control device is configured to receive and evaluate the measurement values determined by the sensors.

Furthermore, the above-mentioned object is achieved by a method for controlling the previously described drinking water supply system, comprising the following steps:
receiving measurement values, in particular measurement values for one or different properties of the water carried in the drinking water supply system, and
controlling the drinking water supply system as a function of the received measurement values.

Furthermore, the above-mentioned object is achieved according to the invention by a computer program comprising commands the execution of which on at least one processor, in particular of the previously described drinking water supply system, initiates the performance of the previously described method. In particular, the central control device of the drinking water supply system can have a memory on which the computer program is stored, with the execution of the computer program on at least one processor of the control device initiating the performance of the method. The central control device can also comprise a server which enables access to the central control device by means of a client, for example via a web browser, wherein the execution of the computer program can take place on the server side and/or client side.

By identifying measurement values, in particular at different points in the drinking water supply system for one or different properties of the water carried in the drinking water supply system and by evaluating the measurement values in a central control device, it is possible to monitor the operation of the drinking water supply system at a central point such that safe operation of the entire system can be ensured. Furthermore, the described drinking water supply system allows for states of the drinking water supply system, in particular critical states or error states which result only from measurements at one or in particular a plurality of points in the drinking water supply system, to be reliably detected such that for example countermeasures based on the situation can be taken.

The drinking water supply system has a drinking water piping system. The drinking water piping system is understood as the piping system which ensures the drinking water supply of different drinking water tapping points in the drinking water supply system. The drinking water piping system in particular comprises connections suitable for the drinking water pipeline such as pipes, hoses, connection pieces, junctions, etc.

A plurality of drinking water tapping points are connected to the drinking water piping system. A drinking water tapping point is understood as components which are supplied with drinking water via the drinking water piping system and at which drinking water can be taken from the drinking water supply system. Examples of drinking water tapping points are for example taps at wash basins, toilet or urinal flushing systems, water outlets on bath tubs and showers and the like.

The drinking water piping system can have one or a plurality of drinking water lines, in particular one or a plurality of main supply lines which in each case feed one or a plurality of subordinate supply lines, into which drinking water tapping points are in each case integrated. If, for example, it is a drinking water supply system of a hospital, a plurality of subordinate supply lines connected to a main supply line can thus for example be provided which in each case supply a ward or facility of the hospital with drinking water. A line of the drinking water piping system preferably comprises in each case a hot water and cold water line. A line can, however, also comprise a plurality of hot water and/or cold water lines.

Furthermore, the drinking water supply system has one or a plurality of sensors preferably configured to determine measurement values for one or different properties of the water carried in the drinking water supply system at different points of the drinking water supply system. The sensors can in particular be integrated into the drinking water piping system and/or into the drinking water tapping points. Examples of sensors integrated into the drinking water piping system are for example pressure, volume flow or temperature sensors and the like which are for example integrated into a pipeline or a fitting. Examples of sensors integrated into a drinking water tapping point are accordingly temperature, pressure or volume flow sensors and the like which are integrated into a mounting of a wash basin or a bath tub or shower or into a cistern of a WC or the supply line of a urinal.

The sensors can in particular be configured to determine measurement values for physical parameters, such as for example the water pressure, the water temperature, the volume flow, the speed distribution of the water or the degree of clouding due to suspended solids, for chemical parameters, such as for example the pH value, the conductivity, the water hardness or the concentration of certain contents, for example the oxygen concentration, or for biological parameters such as for example the germ concentration, in particular the bacteria concentration, in the water.

The drinking water supply system further has a central control device. The central control device can for example comprise a controller with a microprocessor. Furthermore, the control device can also have a plurality of different components which are optionally also remote from one another and connected to one another by a communication connection, such as for example a controller and an associated front end or a further computer and/or a server and a plurality of clients. The central control device itself can in particular be constructed with a decentralised structure, for example with a plurality of equal components in order to increase the reliability.

The central control device is configured to receive the measurement values determined by the sensors. For this purpose, the central control device is in particular connected to the sensors via communication connections. The sensors can for example be connected to the control device in a star shape or also via a bus system, in particular a field bus system. In addition to wired communication connections, wireless communication connections are also conceivable which are advantageous in particular in the case of retrofitting or expanding the drinking water supply system since the installation of lines from a new sensor to a central control device can be at least partially dispensed with.

The central control device is further configured to evaluate the measurement values determined by and received from the one or the plurality of sensors. In particular, the control device can be configured to combine measurement values of different sensors or calculate variables which are dependent on the measurement values of different sensors.

Different embodiments of the drinking water supply system, the method for controlling the same, and the computer program, are described in the following, with the individual embodiments in each case being applicable separately to the drinking water supply system, the method and the computer program. Furthermore, the described embodiments can be combined with one another.

In an embodiment, one or a plurality of the sensors are configured to determine measurement values for the water temperature, the water pressure, the water flow and/or the speed distribution of the water carried in the drinking water supply system. In a corresponding embodiment of the method, measurement values are determined for the water temperature, the water pressure, the water flow and/or the speed distribution of the water carried in the drinking water supply system. In this manner, important parameters can be monitored for the proper functioning of the drinking water supply system at a central point.

By monitoring the water temperature, it can in particular be monitored whether predefined temperature limit values are complied with for the hot and/or the cold water supply. For example, certain standards prescribe a hot water temperature of at least 55° C. and a cold water temperature of at most 25° C. If the water temperatures deviate from this in a hot or cold water line of the drinking water piping system, this can be established at a central point such that corresponding countermeasures can be taken, if necessary. By providing temperature sensors at different points of the drinking water supply system, it is also possible to quickly detect local deviations from target specifications.

By monitoring the water pressure, it can in particular be monitored whether the pressure in a piping section is within predefined limit values. An excessively high pressure can disadvantageously affect the lifetime of the drinking water piping system or components connected thereto. An excessively low pressure may lead to some drinking water tapping points not being adequately supplied. By providing pressure sensors at different points of the drinking water supply system, it is also possible to control the pressure calibration at different locations, for example in different floors. Furthermore, monitoring the pressure can be used to determine leaks in the drinking water supply system early. If, for example, the pressure at different points in the drinking water piping system is monitored for an extended time and the pressure at one point suddenly drops more than usual, this may indicate a leak in the corresponding piping section.

By monitoring the water flow, it can in particular be monitored whether certain piping sections are used particularly frequently or particularly seldom. Furthermore, blockages or constrictions in the piping system can be detected early in this manner. Moreover, it can be monitored, whether in a certain pipeline sufficient water exchange takes place in order to prevent contamination for example. Water flow is understood in the present case as the quantity of water per unit of time, i.e. the quantity of water which flows in a predefined time (e.g. per second, per hour or even per day) through the piping section monitored by the water flow sensor.

By monitoring the speed distribution, it can in particular be monitored whether the water flows in a laminar or turbulent manner through a certain piping section. For this purpose, a plurality of sensors can be arranged behind one another, for example in a piping section, which measure the local speed of the water at different locations of the piping section. A strong fluctuation in speeds from sensor to sensor can be for example an indication of a turbulent current. Furthermore, sensors can be used which measure the speed of the water at different positions in the cross-section of a piping section.

If the water in a piping section flows turbulently, this may lead to the piping section in question also not being fully flushed with sufficient water flow. By monitoring the speed distribution, such a state can be detected and, if appropriate, countermeasures can be taken.

Conversely, a turbulent current may be desired for specific flushing operations since the vortex of a turbulent current can scrape off deposits on the pipe wall of a piping section, in particular a biofilm.

In an embodiment, one or a plurality of sensors are configured to determine measurement values for the drinking water quality of the water carried in the drinking water supply system, in particular for the pH value, for the oxygen concentration, for the concentration of free chlorine, for the water hardness, for the conductivity and/or for the presence or the concentration of certain contents such as for example suspended solids, viruses or micro-organisms, in particular bacteria. In a corresponding embodiment of the method, measurement values are determined for the drinking water quality of the water carried in the drinking water supply system, in particular for the pH value, for the oxygen concentration, for the concentration of free chlorine, for the water hardness, for the conductivity and/or for the presence or the concentration of certain contents such as for example suspended solids, viruses or micro-organisms, in particular bacteria. In this manner, the drinking water quality of the water can be monitored directly. In particular, it can be established early at a central point if the drinking water for example in a certain piping section drops below the predefined quality requirements, such that countermeasures can be taken, before the drinking water quality enters a range critical to health.

The drinking water quality is determined by the contents (e.g. suspended solids, chemical contents, germs such as viruses or micro-organisms) and the chemical and biological properties of the drinking water. In particular, there are many legal limit values for certain contents, which must necessarily be complied with in the drinking water supply. Moreover, special requirements, for example from special operators of the drinking water system such as for example hospitals and the like, may also specify even stricter limit values for the drinking water quality than the legal limit values.

In order to measure the pH value, a pH meter, for example based on the principle of the potentiometry, can be used. In order to measure the water hardness, a photometer can be used for the water hardness determination. In order to measure the conductivity, an ohmmeter can be used.

The monitoring of the pH value, the water hardness and/or the conductivity is relevant in particular also for the lifetime of the system installation, in particular the drinking water piping system. A drinking water installation is typically designed for a certain pH range and a certain water hardness and may suffer damage, frequently fail or have a shorter lifetime if the drinking water is outside of the predefined range.

For example, intense corrosion results in the case of Cu pipelines if the drinking water is too acidic. By monitoring the pH value or the conductivity, measures can be taken in good time in order to counteract this problem of corrosion, for example by flushing the piping system or individual sections thereof. Additionally or alternatively, maintenance intervals can be reduced, Cu pipes can be replaced with acid-resistant pipes and/or water treatment systems can be put into operation.

A higher ion or salt content in the drinking water, which manifests e.g. in an increased conductivity, can disrupt the operation of certain components such as for example an optionally provided softener system. Furthermore, a high degree of hardness of the drinking water can lead to lime deposits. By monitoring the pH value and/or the degree of hardness, measures can be taken in good time in order to counteract these problems, for example by flushing the piping system or individual sections thereof. Additionally or alternatively, maintenance intervals can be reduced and/or water treatment systems put into operation.

In order to measure the presence or the concentration of certain contents, different sensors can be used depending on the content. For example, an optical sensor can be used in order to measure the turbidity of the water due to suspended solids contained therein. Furthermore, a bacteria sensor can be used to determine a value for the number of bacteria in a predefined volume of water, i.e. for the bacteria concentration. Furthermore, sensors can be used to determine the concentration of certain chemical compounds, for example organic compounds, in the water. In order to determine a virus or micro-organism, in particular a bacteria concentration, sensors from the company Roche can for example be used (e.g. CEDEX or CASY analysers). In particular, lab-on-a-chip sensors can also be used.

By monitoring the presence or the concentration of certain contents, compliance with the predefined limit values for certain contents can be monitored at different points in the drinking water supply system. As a result, deviations of a microbiological, chemical or physical type can be determined early.

In particular, sensors can also be provided for determining measurement values for the drinking water quality in the region of a central feed point of the local water supplier into the drinking water supply system. In this manner, the drinking water quality of the water fed into the drinking water supply system can be monitored.

In an embodiment, the control device is configured to cause the output of a piece of user information dependent on the received measurement values via a user interface. In a corresponding embodiment of the method, a piece of user information dependent on the received measurement values is output.

For example, the control device can be configured to monitor the measurement values received from the sensors in regard to an exceedance of or a falling below a limit value or respective limit values and, in case of an exceedance of or falling below a limit value, where applicable over a predefined time period, to output a corresponding warning notification via the user interface.

A limit value for monitoring received measurement values can be fixedly predefined or even determined, in particular by the central control device. In particular, it is conceivable to determine a limit value from previously determined measurement values which have been collected for example over a predefined time period. In this manner, deviations from normal values or value ranges of the past can be determined. Furthermore, it is conceivable to determine measurement values, in particular for the drinking water quality or generally for the composition of the water, at the central feed point of the local water supplier and to determine a limit value as a function thereof. Such a limit value can be compared in particular with corresponding measurement values which have been determined inside the drinking water supply system, in particular at one or a plurality of points in the drinking water piping system. In this manner, changes can be monitored in the water in the drinking water supply system, in particular in the drinking water piping system.

The monitoring of the oxygen content allows detecting in particular points of corrosion in the drinking water supply system, in particular in the drinking water piping system, early. The corrosion process draws oxygen from the water and as a result leads to a drop in the oxygen content. A measurement value determined for the oxygen concentration is preferably monitored to determine whether it falls below a limit value and if it falls below the limit value, a warning notification is output to indicate possible corrosion.

The monitoring of the water hardness makes it possible to establish in particular whether a softener provided in the drinking water supply system is working reliably. A measurement value determined for the water hardness is preferably monitored to determine whether it exceeds a limit value and if it exceeds the limit value, a warning notification is output to indicate a possible defect with the softener.

The monitoring of the concentration of free chlorine makes it possible to determine in particular whether there is contamination of germs in the drinking water supply system. Since free chlorine reacts with germs, contamination of germs leads to a decline in the concentration of free chlorine. A measurement value determined for the concentration of free chlorine is preferably monitored to determine whether it falls below a limit value and if it falls below the limit value, a warning notification is output to indicate possible contamination. The limit value can in particular be determined as a function of a measurement value for the concentration of free chlorine determined at the central feed point of the local water supplier. In this manner, it can be monitored whether the concentration of free chlorine inside the drinking water supply system drops.

The monitoring of the conductivity makes it possible for example to establish to what extent a sacrificial anode provided in the drinking water supply system, for example a sacrificial anode in a hot water unit, is attacked by corrosion. In this manner, the expected lifetime of a sacrificial anode can for example be determined or it can be determined whether a sacrificial anode is exhausted. A measurement value determined for the conductivity is preferably monitored to determine whether it exceeds a limit value.

Furthermore, the control device can be configured to determine a monitoring variable from the measurement values of a plurality of sensors and to indicate, via the user interface, said monitoring variable or the fact it has exceeded or fallen below predefined limit values.

The user interface can for example be a screen. Alternatively, the drinking water supply system can also be configured to send an email or other text message, for example via a mobile communication system, with a corresponding piece of user information.

In a further embodiment, the drinking water supply system has a plurality of decentralised control elements which are configured to influence one or a plurality of properties of the water carried in the drinking water supply system at different points in the drinking water supply system and the central control device is configured to actuate the control elements to influence the one or plurality of properties of the water carried in the drinking water supply system. In a corresponding embodiment of the method, decentralised control elements are actuated to influence one or a plurality of properties of the water carried in the drinking water supply system. In this manner, the water carried in the drinking water supply system can be influenced from a central point.

In an embodiment, one or a plurality of the decentralised control elements are configured to influence the water temperature, the water pressure, the water flow and/or the speed distribution of the water carried in the drinking water supply system and the central control device is configured to actuate the one or plurality of the decentralised control elements to influence the water temperature, the water pressure, the water flow and/or the speed distribution of the water carried in the drinking water supply system. In a corresponding embodiment of the method, decentralised control elements are actuated to influence the water temperature, the water pressure, the water flow and/or the speed distribution of the water carried in the drinking water supply system.

Actuatable mountings can in particular be provided as decentralised control elements. Mountings are understood as components by means of which flows of media can be changed, in particular reduced, redirected or shut off. Examples of mountings are valves such as circulation valves or regulating valves.

The decentralised control elements may for example be actuatable valves, for example flow control or regulating valves, actuatable junctions to redirect a water flow, pumps to influence the water pressure or the current speed of the water, heating or cooling elements to influence the water temperature and the like.

By configuring the central control device to actuate the control elements to influence the water temperature, the water pressure, the water flow and/or the speed distribution, a central control of the drinking water supply system is possible such that the water flow in the entire drinking water supply system can preferably be controlled from one point.

In a further embodiment, one or a plurality of the decentralised control elements are configured to influence the drinking water quality of the water carried in the drinking water supply system, in particular the pH value, the oxygen concentration, the concentration of free chlorine, the water hardness, the conductivity and/or the presence or the concentration of certain contents, such as for example suspended solids, viruses or micro-organisms and the central control device is configured to actuate the one or plurality of the decentralised control elements to influence the drinking water quality of the water carried in the drinking water supply system, in particular the pH value, the water hardness, the conductivity and/or the presence or the concentration of certain contents, such as for example suspended solids, viruses or micro-organisms. In a corresponding embodiment of the method, decentralised control elements are actuated to influence the drinking water quality of the water carried in the drinking water supply system, in particular the pH value, the oxygen concentration, the concentration of free chlorine, the water hardness, the conductivity and/or the presence or the concentration of certain contents such as for example suspended solids, viruses or micro-organisms. In this manner, the drinking water quality of the drinking water supply system can be influenced. In particular, actuating the decentralised control elements allows the drinking water quality to remain in the desired range in the entire drinking water supply system.

In order to regulate the pH value, flushing operations can in particular be carried out in which the piping system or sections thereof are flushed with water. If the pH value is outside of a predefined range, a user alarm is further preferably output via a provided user interface, since such a change in the pH value is rather unusual, such that such an incident should be checked carefully.

A water softener can for example be provided to influence the water hardness. Filters can for example be provided to remove suspended solids or bacteria in the water. Furthermore, a sterilisation segment for the thermal treatment of the water or to irradiate the water with UV light can be provided to kill bacteria.

The water softener, the filter or the sterilisation segment can for example be provided in a separate piping section which is connected to a pipeline of the drinking water piping system via actuatable valves. By actuating the valves, the water can be redirected through the separate piping section in a specific manner and therefore directed through the water softener, the filter or the sterilisation segment.

In a further embodiment, the central control device is configured to receive a piece of information about the time of the day and to actuate the control elements to influence the one or plurality of properties of the water carried in the drinking water supply system as a function of the piece of information received about the time of the day. In a corresponding embodiment of the method, control elements are actuated to influence the one or plurality of properties of the water carried in the drinking water supply system as a function of a piece of information about the time of the day. In this manner, the control of the drinking water supply system can be adapted to the varying requirements at different times of the day. For example, different control programs can be provided for the day and for the night. In order to obtain the piece of information about the time of the day, a clock, for example a system clock, is preferably provided in the central control device. The receipt of the piece of information about the time of the day does not therefore require the piece of information to be provided from outside of the central control device.

In a further embodiment, a plurality of control elements are combined to form a virtual group and the control device is preferably configured to actuate the individual control elements of the virtual group, preferably according to an actuation plan predefined for the group, when a command is received to actuate the virtual group. In a further embodiment of the method, a command to actuate a virtual group, where appropriate according to a predefined actuation plan, is received and the individual control elements of the virtual group are actuated, in particular according to the predefined actuation plan.

In this manner, a simpler control of the drinking water supply system is achieved since it is no longer necessary to actuate all the control elements individually, but rather a groupwise actuation is enabled.

If the drinking water supply system for example has a drinking water line with a plurality of drinking water tapping points at which in each case control elements are provided to automatically drain drinking water out of the drinking water supply system, these control elements can thus be combined into a virtual group and then actuated together by means of an individual command. For example, in this manner, a certain section of the drinking water supply system can be flushed by means of a single user command.

Furthermore, a plurality of flow control and/or junction valves, which regulate the supply of a certain drinking water line, can be combined into a group, such that they can be opened and closed together.

An actuation plan is preferably defined which contains the commands to be output to the individual control elements of the virtual group. Furthermore, the actuation plan can contain information regarding the times at which the individual control elements are to be actuated, for example the sequence of the actuation.

The drinking water supply system can have a plurality of decentralised control devices, for example a plurality of controllers, which are connected in each case to one or a plurality of decentralised control elements for control thereof. The decentralised control devices are connected directly or indirectly to the central control device such that the central control device, by actuating the respective decentralised control devices, can initiate control of the decentralised control elements connected therewith in each case.

A virtual group can in particular comprise decentralised control elements which are assigned to different decentralised control devices. The virtual grouping of control elements allows, in this manner, a grouping of control elements overlapping the individual decentralised control devices irrespective of the hardware architecture, i.e. of the respective assignment of control elements to certain decentralised control devices.

Decentralised control elements can preferably be assigned to a virtual group via the central control device, for example by means of a corresponding user input via a user interface of the central control device. In this manner, a virtual group can be flexibly set on the software side without hardware-side changes being required, such as for example connecting a control element to another decentralised control device.

In a further embodiment, an actuation plan is predefined which contains a plurality of actuation commands for different control elements and the control device is configured to actuate the control elements according to the actuation plan when a command is received to carry out the predefined actuation plan. In a corresponding embodiment of the method, an actuation plan is predefined which contains a plurality of actuation commands for different control elements, a command is received to carry out the predefined actuation plan and the control elements are actuated according to the actuation plan.

In this manner, the control of the drinking water supply system is simplified by the user being able to process a possibly complex command sequence by inputting an individual command or retrieving the actuation plan, which for example actuates different control elements at different times.

In a further embodiment, the drinking water piping system has a cold water line for the cold water supply of a plurality of drinking water tapping points, with a supply line, which supplies the cold water line with cold water, being connected to a first end of the cold water line, and with a circulation line being connected to a second end of the cold water line, via which water can be discharged from the cold water line. The drinking water piping system can have a plurality of cold water lines, with one, a plurality of or all cold water lines being able to be connected, as previously described, to a circulation line.

In the cold water supply, there is the problem that impurities and contamination of germs can form in a cold water line if the drinking water tapping points provided on the cold water line are not actuated sufficiently such that the water stays in the cold water line for a long time. In particular, the water remaining in the cold water line for a long time can be heated above a certain temperature, whereby contamination of germs (germ growth) is further promoted. Providing a circulation line for the cold water line allows cold water to be exchanged in a cold water line inside the drinking water supply system even if the drinking water tapping points are not actuated or only actuated occasionally.

The circulation line is preferably connected such that it leads the water carried therein back into the rest of the drinking water piping system such that it can be used further.

In a further embodiment, a control element is integrated into the drinking water piping system, preferably an actuatable valve configured to control the discharge of water from the cold water line via the circulation line (circulating). For example, such a valve can be arranged at the transition from the cold water line to the circulation line. By providing an actuatable valve, a controllable cold water circulation is enabled. By opening the valve, water can be directed out of the cold water line such that the water does not remain in the cold water line for too long. Otherwise, when closing the valve, the water can be prevented from circulating unnecessarily or the pressure in the drinking water supply system can be prevented from decreasing too much. The control device is preferably configured to control the control element.

The drinking water piping system can be configured such that water is continuously circulated in the cold water line, for example by an actuatable valve in the cold water line allowing a minimal quantity of water to pass even in the closed state. In this manner, local heat input not detectable by the available sensors can also be avoided.

In a further embodiment, the drinking water piping system has a cold water line for the cold water supply of a plurality of drinking water tapping points and the drinking water piping system has a cooling segment for water cooling which is connected to the cold water line in order to cool water from the cold water line. The drinking water piping system can have a plurality of cold water lines, with one, a plurality or all cold water lines being able to be connected, as previously described, to the water cooling system.

It has been found that the temperature of the water in a cold water line can be raised in the case of excessively long dwell times in the cold water line or also in the case of excessively high ambient temperatures to such an extent that an increased contamination of germs is promoted. By providing a cooling segment, the undesirably heated water from the cold water line can be cooled such that contamination of germs caused by the heating can be counteracted.

In a further embodiment, the cooling segment has an active cooling element, for example a heat exchanger driven by means of a coolant. This allows an efficient and quick cooling of the water directed through the cooling segment.

In a further embodiment, the cooling segment has a piping section which is laid through a region with a lower average temperature than the cold water line. The average temperature may for example be the daily, monthly or yearly average temperature. For example, the cooling segment can have a piping section which is guided through a cellar space or through the soil since these regions typically have a lower average temperature than common rooms for people, for example. This embodiment allows a particularly energy-saving cooling of the water since active cooling units are not required.

In a further embodiment, the drinking water piping system has a cold water line for the cold water supply and a hot water line for the hot water supply and a heat pump is provided in order to transport heat from the water carried in the cold water line to the water carried in the hot water line. The heat pump is thus configured to transport heat from the water carried in the cold water line to the water carried in the hot water line. As a result, cooling of the water in the cold water line and heating of the water in the hot water line are achieved simultaneously in an economical manner. The heat pump can for example be actuated if the water temperature in the cold water line is too high or the water temperature in the hot water line is too low.

In a further embodiment, the drinking water piping system has a hot water piping system with a hot water main supply line and a plurality of hot water secondary lines departing therefrom, a central hot water unit is provided which is configured to feed hot water into the hot water main supply line and a decentralised hot water unit is provided which is assigned to one of the plurality of hot water secondary lines and is configured to heat water introduced from the hot water main supply line into the hot water secondary line to which the decentralised hot water unit is assigned.

In this manner, water can be heated in a hot water secondary line without the water having to be led back into the central hot water unit, which is possibly far away. If, for example, in a large building complex such as a hospital, a central hot water unit is provided, the hot water must, under certain circumstances, cover a long path from the central hot water unit until reaching a hot water line in a remote part of the building. As a result, the hot water, when it reaches the hot water secondary line, can already be cooled to the extent that, after a short time, it falls below a predefined minimum temperature, for example below 55° C. and must be pumped back to the central hot water unit. By providing a decentralised hot water unit, the water can be reheated such that it has an adequate temperature again. The decentralised hot water unit can for example be arranged between the junction from the hot water main supply line to the hot water secondary line and the first drinking water tapping point of the hot water secondary line.

Since the decentralised hot water unit has to heat only the quantity of water for the hot water secondary line and since water already preheated by the central hot water unit is heated, meaning a smaller temperature increase has to be achieved, the decentralised hot water unit can be designed correspondingly smaller and more compactly than the central hot water unit. For example, the central hot water unit can be designed for the quantity of water to supply the entire drinking water supply system and to heat the water from 20° C. to 65° C., while the decentralised hot water unit must be designed only for the quantity of water to supply the hot water secondary line and to heat the water from 50° C. to 65° C.

In a further embodiment, the drinking water piping system has a drinking water line and a flushing unit that is actuatable by the central control device is integrated into the drinking water line, through which flushing unit water can be drained from the drinking water supply system. The flushing unit can for example be an actuatable drinking water tapping point which is actuatable such that water can be drained from the drinking water supply system. Alternatively, a separate flushing unit can also be provided, whose single object is to drain drinking water from the drinking water supply system in the event of corresponding actuation. Such a separate flushing unit allows the water in the drinking water line to be exchanged, for example if it has become too hot or cold there or has been there for too long. The drinking water line may be a hot water line or a cold water line.

In a further embodiment, a decentralised control unit that is actuatable by the central control device is provided which is configured to initiate a flushing operation at a drinking water tapping point in order to drain water from the drinking water supply system. In this manner, a drinking water tapping point, for example a tap at a wash basin or a WC flushing system, can be centrally actuated in order to drain water from the drinking water supply system.

The central control device is preferably configured, by actuating one or a plurality of decentralised control units at a plurality of drinking water tapping points, to simultaneously initiate a flushing operation, with the plurality of drinking water tapping points preferably being connected to the same line or the same pipeline of the drinking water piping system. The drinking water tapping points may, for example, be adjacent to one another. In this manner, during the flushing operations, a higher flow speed can be achieved inside the line or the pipeline such that a turbulent current is produced whose vortex enables improved cleaning of the pipe wall, for example of a biofilm.

The central control device is preferably configured to control the performance of flushing operations at a drinking water tapping point as a function of a piece of information about the time of the day. In this manner, automatic flushing at night can for example be prevented if the drinking water tapping point in question is located for example in a hospital ward or is especially performed during the night if the drinking water tapping point in question is located for example in an office wing that is unstaffed at night.

In a further embodiment, an acoustic sensor is provided which is configured and/or arranged to measure measurement values for the volume level, in particular for the volume level of one or a plurality of flushing operations at one or a plurality of drinking water tapping points, and the central control device is preferably configured to control the automatic performance of flushing operations as a function of the measurement values measured by the acoustic sensor. In this manner, in the case of the automatic performance of flushing operations, the associated noise level can be monitored such that flushing operations can, for example, be interrupted or prevented if a predefined noise level is exceeded. The predefined noise level is preferably selected as a function of the location and/or time of the day.

In a further embodiment, a presence detector is provided which is configured to determine a piece of information about the presence of a person, and the central control device is preferably configured to control one or a plurality of the decentralised control elements as a function of the piece of information about the presence of a person. In this manner, the drinking water supply system can be controlled as a function of whether or not persons are present for example in the region of a certain drinking water line or certain drinking water tapping points. If the presence detector determines for example the presence of persons, a different need for drinking water is to be expected in the determined drinking water line or at the determined drinking water tapping point than without persons. The presence detector can for example be a motion detector or also a camera whose images are analysed by means of person recognition algorithms.

In a further embodiment, the central control device is configured to control the drinking water supply system, in particular the decentralised control elements, selectively according to a first predefined program or according to a second predefined program, and the central control device is further configured to select the first or the second program as a function of the piece of information about the presence of a person. The first program can for example be a program for a normal mode and the second program can be an absence program, for example a holiday program. In this manner, the central control system can automatically switch between a normal mode and an absence mode, for example a holiday mode without the user having to make a corresponding user input. Naturally, the central control device can be configured to select between more than two programs as a function of the piece of information about the presence of a person.

In a further embodiment, a decentralised control unit that is actuatable by the central control device is provided which is configured to initiate a flushing operation at a drinking water tapping point in order to drain water from the drinking water supply system, the presence detector is configured and arranged to determine a piece of information about the presence of a person in the region of the drinking water tapping point and the central control device is configured to control the performance of a flushing operation at the drinking water tapping point as a function of the piece of information about the presence of a person. In this manner, the safety can be improved during the automatic control of the drinking water supply system. In particular, an automatic flush at a drinking water tapping point can be interrupted or prevented if it is determined that a person is located in the region of the drinking water tapping point. As a result, the person in question can be prevented from becoming unexpectedly wet due to draining water or possibly even prevented from being scalded in the case of draining hot water.

In a further embodiment, the drinking water piping system has a drinking water line, a group of drinking water tapping points is provided which are connected to the drinking water line, a plurality of decentralised sensors are provided which are configured to determine information about the performance of flushing operations at drinking water tapping points of the group of drinking water tapping points and the central control device is configured to control the performance of flushing operations at individual drinking water tapping points of the group of drinking water tapping points as a function of the information about the performance of flushing operations at drinking water tapping points of the group of drinking water tapping points.

The control elements provided for the performance of flushing operations at the individual drinking water tapping points can in particular be combined into a virtual group.

In this manner, the central control device can monitor for an entire drinking water line with a plurality of drinking water tapping points whether the drinking water line is adequately flushed by actuating one of the drinking water tapping points and if this is not the case, a corresponding flush can be caused by an automatic flush at some of the drinking water tapping points. Compared with autonomously controlled drinking water tapping points, which automatically perform flushing operations if they are not actuated for a predefined time, this has the advantage that the central control device monitors the entirety of the drinking water tapping points such that an automatic flush at a drinking water tapping point can be avoided if, for example, an adjacent drinking water tapping point has been recently flushed. Furthermore, when a flush is required, individual drinking water tapping points can be actuated instead of all drinking water tapping points. The flushing volume and the frequency of flushing operations is hereby reduced such that water can be saved.

In a further embodiment, one or a plurality of decentralised sensors are provided which are configured to determine information about the performance of flushing operations in a predefined section of the drinking water piping system and the central control device is configured to monitor the time since the last flush in the predefined section of the drinking water piping system and to cause a flush in the predefined section of the drinking water piping system when a predefined maximum time duration is exceeded. In this manner, it can be centrally monitored whether a section of the drinking water piping system is flushed often enough and, if this is not the case, it is automatically flushed.

In a further embodiment, the central control device is configured to control the control elements as a function of the received measurement values. In this manner, regulation of the drinking water supply system is enabled. As a result, permanent operation can for example be achieved within a safe parameter window, for example by deviations from the target range being automatically counteracted.

In a further embodiment, the drinking water piping system has a cold water line for the cold water supply of a plurality of drinking water tapping points, a temperature sensor is provided in order to measure the water temperature of the water in the cold water line and the control device is configured to initiate a measure if the temperature measured by the temperature sensor exceeds a predefined limit value. In order to measure the water temperature of the water in the cold water line, the temperature sensor can in particular be integrated into the cold water line or into a drinking water tapping point connected to the cold water line. In the corresponding embodiment of the method, a measure is initiated if a temperature measured by a temperature sensor in a cold water line exceeds a limit value.

The measure may in particular be the cooling of the water from the cold water line in a cooling segment. Furthermore, the measure may be the draining of the water from the cold water line at a flushing unit. Furthermore, the measure may be the discharging of the water from the cold water line via a circulation line.

By initiating one or a plurality of these measures, the increased temperature in the cold water line is counteracted such that imminent contamination of germs can be prevented. By cooling the water, the temperature of the water is reduced further such that germ formation is effectively prevented. By draining the water at a flushing unit, the water that would be imminently contaminated with germs is drained from the drinking water supply system such that fresh water can subsequently flow into the cold water line. By the discharging of the water via a circulation line, the water is discharged from the cold water line such that the next flow of fresh water enters the cold water line. Unlike in the case of draining the water at a flushing unit, the water discharged via the circulation line preferably remains in the drinking water supply system and can be reused at another point.

The drinking water piping system can be configured such that the drinking water discharged from the cold water line is channeled to a hot water unit for the hot water supply, for example by means of an actuatable three-way valve, in particular if, in accordance with the previously described embodiment, the temperature measured by a temperature sensor to measure the temperature in the cold water line exceeds a predefined limit value. In this manner, the water from the cold water line, which could for example have an increased bacteria content due to heating, can be safely reused inside the system since the bacteria are killed by the heat treatment in the hot water unit.

Alternatively, the drinking water discharged from the cold water line can essentially be guided to the hot water unit.

Furthermore, the measure may be the output of a user notification. Through the output of a user notification, a person in charge can be informed of an imminent contamination of germs.

In a further embodiment, the drinking water piping system has a hot water line for the hot water supply of a plurality of drinking water tapping points, a temperature sensor is provided in order to measure the water temperature of the water in the hot water line and the control device is configured to initiate a measure if the temperature measured by the temperature sensor falls below a predefined limit value. In order to measure the water temperature of the water in the hot water line, the temperature sensor can in particular be integrated into the hot water line or into a drinking water tapping point connected to the hot water line. In the case of the corresponding embodiment of the method, a measure is initiated if the temperature measured by a temperature sensor in a hot water line falls below a predefined limit value.

The measure may in particular be the draining of the water from the hot water line at a flushing unit. Draining can of course also take place at a plurality of flushing units. Furthermore, the measure may be the discharging of the water from the hot water line via a circulation line. Furthermore, the measure may be the output of a user notification.

If the temperature in a hot water line drops too low, increased germ formation may result since the water temperature is no longer sufficient to kill bacteria and the like.

By draining the water from the hot water line, this water is removed from the drinking water supply system so that fresh, sufficiently hot water can subsequently flow into the hot water line. Accordingly, in the case of discharging the water from the hot water line via a circulation line, the water is discharged from the hot water line so that correspondingly hot water can subsequently flow in. The water preferably still remains available in the drinking water supply system in the case of discharging via a circulation line and can therefore be reused at another point, for example reheated in a correspondingly provided unit. Through the output of a user notification, a person in charge can be informed of an imminent contamination of germs.

In a further embodiment, the drinking water piping system has a drinking water line for the drinking water supply of a plurality of drinking water tapping points, a volume flow sensor is provided in order to measure the volume flow of the water in the drinking water line and the control device is configured to determine a value for the water volume which has flowed within a predefined time through the volume flow sensor as a function of the volume flow measured by the volume flow sensor, and to initiate a measure when the value for the water volume falls below a predefined limit value. In order to measure the volume flow of the water in the drinking water line, the volume flow sensor can in particular be integrated into the drinking water line. In a corresponding embodiment of the method, a value is determined, as a function of a volume flow measured by a volume flow sensor in a drinking water line, for the water volume which has flowed through the volume flow sensor within a predefined time and a measure is initiated when the value for the water volume falls below a predefined limit value.

The measure may in particular be the draining of the water from the drinking water line at a flushing unit. Draining can of course also take place at a plurality of flushing units. Furthermore, the measure may be the discharging of the water from the drinking water line via a circulation line. Furthermore, the measure may also be the output of a user notification.

If the volume flowing through the volume flow sensor falls below a limit value, this indicates that too little water is being removed from the drinking water line and that the drinking water has therefore been in the drinking water line for too long. By draining or discharging the water from the drinking water line, the volume exchange can be automatically initiated so that fresh water can subsequently flow into the drinking water line.

Furthermore, an excessively low volume flow can also indicate that a certain drinking water tapping point or group of drinking water tapping points are used less than other drinking water tapping points. This can for example indicate a defect in the corresponding drinking water tapping point, for example a defective WC. Through the output of a user output, a caretaker, for example, can then be made aware of the fact that a certain WC is not being used so that he can check whether there is possibly a need for repair.

The predefined limit value can for example be calculated as a function of the values of volume flow sensors at different drinking water lines or drinking water tapping points. In this manner, it can be determined if the removal in a determined region of a drinking water line or at a determined drinking water tapping point is unusually high or unusually low such that corresponding measures can be taken.

In a further embodiment, the drinking water piping system has a drinking water line for the drinking water supply of a plurality of drinking water tapping points, a volume flow sensor is provided in order to measure the volume flow of the water in the drinking water line and the control device is configured to initiate a measure if the volume flow measured by the volume flow sensor exceeds a predefined limit value. In order to measure the volume flow of the water in the drinking water line, the volume flow sensor can in particular be integrated into the drinking water line. In a corresponding embodiment of the method, a measure is initiated when the volume flow measured by a volume flow sensor in a drinking water line exceeds a predefined limit value.

The measure may in particular be the increase of the water pressure, for example by activation or increase of the output of a water pump provided in the drinking water supply system to increase the flow and/or pressure in the drinking water line or by opening a supply line valve through which more water is supplied to the drinking water line in question. Furthermore, the measure may be to end and/or prevent a draining of water from the drinking water line at a flushing unit, said draining being initiated by the central control device. Furthermore, the measure may be to end and/or prevent a discharging of water from the drinking water line via a circulation line, said discharging being initiated by the central control device.

Exceeding a predefined volume flow indicates that the drinking water line is used more heavily than its capacity allows, for example because water is removed at too many drinking water tapping points at the same time. This may lead to the water flow or the pressure decreasing at the individual water tapping points such that the drinking water tapping points can possibly no longer be used correctly.

By increasing the water pressure, in particular by the activation or increase of the output of a water pump provided in the drinking water supply system or by the opening of a supply line valve, the flow or the pressure can be increased in the drinking water line such that even when the drinking water line is used more heavily, the water supply is still ensured. The pressure or flow increase can in particular be limited to the time period in which there is an overloading of the drinking water line, for example in order to save power or to reduce the mechanical strain on the drinking water line.

Ending and/or preventing draining or discharging of water from the drinking water line, said measure(s) being initiated by the central control device, can prevent the pipeline pressure or the quantity of water available for the water supply, from being reduced further by such a centrally controlled removal of water from the drinking water line, such that more water or a higher pressure remains for the other drinking water tapping points.

Furthermore, the measure may be the output of a user notification. Through the output of a user notification, a person in charge can be informed for example of a possible bottleneck in the drinking water supply.

If, while water is being discharged from a drinking water line via a circulation line under the control of the central control device, a sudden volume flow increase takes place due to the activation of further drinking water tapping points, for example due to the opening of a plurality of taps, the circulation preferably controlled by the central control device is automatically interrupted.

The measure can preferably be initiated by the control device if the volume flow measured by the volume flow sensor is above a predefined limit value for a predefined time period. In this manner, a possibly unnecessary countermeasure can be prevented from being taken in the case of very brief volume flow changes.

In a further embodiment, the drinking water piping system has a drinking water line for the drinking water supply of a plurality of drinking water tapping points, a pressure sensor is provided in order to measure the water pressure in the drinking water line and the control device is configured to initiate a measure if the water pressure measured by the pressure sensor falls below a predefined limit value. In order to measure the water pressure in the drinking water line, the pressure sensor can in particular be integrated into the drinking water line or into a drinking water tapping point connected to the drinking water line. In a corresponding embodiment of the method, a measure is initiated if the water pressure measured by a pressure sensor in a drinking water line falls below a predefined limit value.

The measure may for example be an increase of the water pressure, in particular by the activation or increase of the output of a water pump provided in the drinking water supply system to increase the flow and/or pressure in the drinking water line or by opening a supply line valve. Furthermore, the measure may be to end and/or prevent a draining of water from the drinking water line at a flushing unit, said measure being initiated by the central control device. Furthermore, the measure may be to end and/or prevent a discharging of water from the drinking water line via a circulation line, said measure being initiated by the central control device.

As in the case of the previously described embodiments, a pressure falling below a minimum value may also be a sign that a drinking water line is overloaded. The described measures allow the overloading of the drinking water line to be cancelled out during the period of strain.

Furthermore, the measure may be the output of a user notification. Through the output of a user notification, a person in charge can be informed for example of a possible bottleneck in the drinking water supply.

The measure is preferably initiated if the water pressure measured by the pressure sensor falls below the predefined limit value for a determined time period in order to prevent possibly unnecessary countermeasures in the case of brief pressure fluctuations.

In a further embodiment, the drinking water piping system has a drinking water line for the drinking water supply of a plurality of drinking water tapping points, a pressure sensor is provided in order to measure the water pressure in the drinking water line and the control device is configured to initiate a measure when the water pressure measured by the pressure sensor exceeds a predefined limit value. In order to measure the water pressure in the drinking water line, the pressure sensor can in particular be integrated into the drinking water line or into a drinking water tapping point connected to the drinking water line. In a corresponding embodiment of the method, a measure is initiated when the water pressure measured by the pressure sensor in a drinking water line exceeds a predefined limit value.

The measure may for example be a reduction of the water pressure, in particular by the deactivation or reduction of the output of a water pump provided in the drinking water supply system to increase the flow and/or pressure in the drinking water line or by closing a supply line valve. Furthermore, the measure may be the draining of the water from the cold water line at a flushing unit. Draining can of course also take place at a plurality of flushing units.

If a plurality of drinking water tapping points are closed at the same time, this may result in a pressure increase in the drinking water line. This can be counteracted using the previously described measures. In this manner, the mechanical strain on the drinking water piping system can be reduced and therefore a longer lifetime can be achieved.

Furthermore, the measure may be the output of a user notification. In this manner, a person in charge of the safe operation of the drinking water supply system may be informed of a possibly critical overpressure.

In a further embodiment, the control device is configured to initiate control of the drinking water supply system according to the previously described method or an embodiment thereof. For example, the control device can have a memory with commands the execution of which on at least one processor of the control device initiates the performance of the previously described method.

Further embodiments 1 to 34 of the drinking water supply system, a further embodiment 35 of the method and a further embodiment 36 of the computer program are described below. These embodiments can be combined both with one another and with the previously described embodiments.

1. Drinking water supply system comprising a drinking water piping system, comprising a plurality of drinking water tapping points connected to the drinking water piping system, comprising at least one sensor configured to determine measurement values and comprising a central control device configured to receive and evaluate the measurement values determined by the at least one sensor.
2. Drinking water supply system according to embodiment 1, with a plurality of sensors being provided which are configured to determine measurement values for one or different properties of the water carried in the drinking water supply system at different points in the drinking water supply system and with the central control device being configured to receive and evaluate the measurement values determined by the sensors.
3. Drinking water supply system according to embodiment 2, with one or a plurality of the sensors being configured to determine measurement values for the water temperature, the water pressure, the water flow and/or the speed distribution of the water carried in the drinking water supply system.
4. Drinking water supply system according to embodiment 2 or 3, with one or a plurality of sensors being configured to determine measurement values for the drinking water quality of the water carried in the drinking water supply system, in particular for the pH value, for the water hardness, for the conductivity and/or for the presence or the concentration of certain contents such as for example suspended solids, viruses or micro-organisms.
5. Drinking water supply system according to any one of embodiments 1 to 4, with the control device being configured to initiate the output of a piece of user information dependent upon the received measurement values via a user interface.
6. Drinking water supply system according to any one of embodiments 1 to 5, with a plurality of decentralised control elements which are configured to influence one or a plurality of properties of the water carried in the drinking water supply system at different points in the drinking water supply system, with the central control device being configured to actuate the control elements to influence the one or plurality of properties of the water carried in the drinking water supply system.
7. Drinking water supply system according to embodiment 6, with one or a plurality of the decentralised control elements being configured to influence the water temperature, the water pressure, the water flow and/or the speed distribution of the water carried in the drinking water supply system, and with the central control device being configured to actuate the one or plurality of the decentralised control elements to influence the water temperature, the water pressure, the water flow and/or the speed distribution of the water carried in the drinking water supply system.
8. Drinking water supply system according to embodiment 6 or 7, with one or a plurality of the decentralised control elements being configured to influence the drinking water quality of the water carried in the drinking water supply system, in particular the pH value, the water hardness, the conductivity and/or the presence or the concentration of certain contents, such as for example suspended solids, viruses or micro-organisms, and with the central control device being configured to actuate the one or plurality of the decentralised control elements to influence the drinking water quality of the water carried in the drinking water supply system, in particular the pH value, the water hardness, the conductivity and/or the presence or the concentration of certain contents, such as for example suspended solids, viruses or micro-organisms.
9. Drinking water supply system according to any one of embodiments 6 to 8, with the central control device being configured to receive a piece of information about the time of the day and actuate the control elements to influence the one or plurality of properties of the water carried in the drinking water supply system as a function of the piece of information received about the time of the day.
10. Drinking water supply system according to any one of embodiments 6 to 9, with a plurality of control elements being combined to form a virtual group and the control device being configured to actuate the individual control elements of the virtual group, preferably according to an actuation plan predefined for the group, when a command is received to actuate the virtual group.
11. Drinking water supply system according to any one of embodiments 6 to 10, with an actuation plan being predefined which contains a plurality of actuation commands for different control elements, and the control device being configured to actuate the control elements according to the actuation plan when a command is received to carry out the predefined actuation plan.
12. Drinking water supply system according to any one of embodiments 1 to 11, with the drinking water piping system having a cold water line for the cold water supply of a plurality of drinking water tapping points, with a supply line supplying the cold water line with cold water being connected to a first end of the cold water line and with a circulation line being connected to a second end of the cold water line, via which water can be discharged from the cold water line.
13. Drinking water supply system according to embodiment 12, with a control element being integrated into the drinking water piping system, preferably an actuatable valve configured to control the discharge of water from the cold water line via the circulation line.
14. Drinking water supply system according to any one of embodiments 1 to 13, with the drinking water piping system having a cold water line for the cold water supply of a plurality of drinking water tapping points and with the drinking water piping system having a cooling segment for water cooling which is connected to the cold water line in order to cool water from the cold water line.
15. Drinking water supply system according to embodiment 14, with the cooling segment having an active cooling element, for example a heat exchanger operated with a coolant.
16. Drinking water supply system according to embodiment 14 or 15, with the cooling segment having a piping section which is laid through a region with a lower average temperature than the cold water line.
17. Drinking water supply system according to any one of embodiments 1 to 16, with the drinking water piping system having a cold water line for the cold water supply and a hot water line for the hot water supply and with a heat pump being provided in order to transport heat from the water carried in the cold water line to the water carried in the hot water line.
18. Drinking water supply system according to any one of embodiments 1 to 17, with the drinking water piping system having a hot water piping system with a hot water main supply line and a plurality of hot water secondary lines departing therefrom, with a central hot water unit being provided which is configured to feed hot water into the hot water main supply line and with a decentralised hot water unit being provided which is assigned to one of the plurality of hot water secondary lines and is configured to heat water introduced from the hot water main supply line into the hot water secondary line, to which the decentralised hot water unit is assigned.
19. Drinking water supply system according to any one of embodiments 1 to 18, with the drinking water piping system having a drinking water line and with a separate flushing unit that is actuatable by the central control device being integrated into the drinking water line, through which flushing unit water can be drained from the drinking water supply system.
20. Drinking water supply system according to any one of embodiments 1 to 19, with a decentralised control unit that is actuatable by the central control device being provided which is configured to initiate a flushing operation at a drinking water tapping point in order to drain water from the drinking water supply system.
21. Drinking water supply system according to embodiment 20, with an acoustic sensor being provided which is configured and arranged to measure measurement values for the volume level of one or a plurality of flushing operations at one or a plurality of drinking water tapping points, and with the central control device being configured to control the automatic performance of flushing operations as a function of the measurement values measured by the acoustic sensor.
22. Drinking water supply system according to any one of embodiments 1 to 21, with a presence detector being provided which is configured to determine a piece of information about the presence of a person, and with the central control device being configured to control one or a plurality of the decentralised control elements as a function of the piece of information about the presence of a person.
23. Drinking water supply system according to embodiment 22, with the central control device being configured to control the drinking water supply system, in particular the decentralised control elements, selectively according to a first predefined program or according to a second predefined program, and with the central control device being further configured to select the first or the second program as a function of the piece of information about the presence of a person.
24. Drinking water supply system according to embodiment 22 or 23, with a decentralised control unit that is actuatable by the central control device being provided which is configured to initiate a flushing operation at a drinking water tapping point in order to drain water from the drinking water supply system, with the presence detector being configured and arranged to determine a piece of information about the presence of a person in the region of the drinking water tapping point and with the central control device being configured to control the performance of a flushing operation at the drinking water tapping point as a function of the piece of information about the presence of a person.
25. Drinking water supply system according to any one of embodiments 1 to 24, with the drinking water piping system having a drinking water line, with a group of drinking water tapping points being provided which are connected to the drinking water line, with a plurality of decentralised sensors being provided which are configured to determine information about the performance of flushing operations at drinking water tapping points of the group of drinking water tapping points and with the central control device being configured to control the performance of flushing operations at individual drinking water tapping points of the group of drinking water tapping points as a function of the information about the performance of flushing operations at drinking water tapping points of the group of drinking water tapping points.
26. Drinking water supply system according to any one of embodiments 1 to 25, with one or a plurality of decentralised sensors being provided which are configured to determine information about the performance of flushing operations in a predefined section of the drinking water piping system, with the central control device being configured to monitor the time since the last flush in the predefined section of the drinking water piping system and to cause a flush in the predefined section of the drinking water piping system if a predefined maximum time duration is exceeded.
27. Drinking water supply system according to any one of embodiments 1 to 26, with the central control device being configured to control the control elements as a function of the received measurement values.
28. Drinking water supply system according to embodiment 27, with the drinking water piping system having a cold water line for the cold water supply of a plurality of drinking water tapping points, with a temperature sensor being provided in order to measure the water temperature of the water in the cold water line and with the control device being configured to initiate one of the following measures if the temperature measured by the temperature sensor exceeds a predefined limit value:

cooling the water from the cold water line in a cooling segment, draining the water from the cold water line at a flushing unit, discharging the water from the cold water line via a circulation line or output of a user notification.

29. Drinking water supply system according to embodiment 27 or 28, with the drinking water piping system having a hot water line for the hot water supply of a plurality of drinking water tapping points, with a temperature sensor being provided in order to measure the water temperature of the water in the hot water line and with the control device being configured to initiate one of the following measures if the temperature measured by the temperature sensor falls below a predefined limit value:

draining the water from the hot water line at a flushing unit, discharging the water from the hot water line via a circulation line or output of a user notification.

30. Drinking water supply system according to any one of embodiments 27 to 29, with the drinking water piping system having a drinking water line for the drinking water supply of a plurality of drinking water tapping points, with a volume flow sensor being provided in order to measure the volume flow of the water in the drinking water line and with the control device being configured to determine a value for the water volume which has flowed within a predefined time through the volume flow sensor as a function of the volume flow measured by the volume flow sensor, and being configured to initiate one of the following measures when the value for the water volume falls below a predefined limit value:

draining the water from the drinking water line at a flushing unit, discharging the water from the drinking water line via a circulation line or output of a user notification.

31. Drinking water supply system according to any one of embodiments 27 to 30, with the drinking water piping system having a drinking water line for the drinking water supply of a plurality of drinking water tapping points, with a volume flow sensor being provided in order to measure the volume flow of the water in the drinking water line and with the control device being configured to initiate one of the following measures if the volume flow measured by the volume flow sensor exceeds a predefined limit value:

increasing the water pressure in the drinking water line, in particular by activating or increasing the output of a water pump provided in the drinking water supply system, ending and/or preventing draining of water from the drinking water line at a flushing unit initiated by the central control device, ending and/or preventing discharging of water from the drinking water line via a circulation line initiated by the central control device or output of a user notification.

32. Drinking water supply system according to any one of embodiments 27 to 31, with the drinking water piping system having a drinking water line for the drinking water supply of a plurality of drinking water tapping points, with a pressure sensor being provided in order to measure the water pressure in the drinking water line, and with the control device being configured to initiate one of the following measures if the water pressure measured by the pressure sensor falls below a predefined limit value:

increasing the water pressure in the drinking water line, in particular by activating or increasing the output of a water pump provided in the drinking water supply system, ending and/or preventing draining of water from the drinking water line at a flushing unit initiated by the central control device, ending and/or preventing discharging of water from the drinking water line via a circulation line initiated by the central control device or output of a user notification.

33. Drinking water supply system according to any one of embodiments 27 to 32, with the drinking water piping system having a drinking water line for the drinking water supply of a plurality of drinking water tapping points, with a pressure sensor being provided in order to measure the water pressure in the drinking water line and with the control device being configured to initiate one of the following measures if the water pressure measured by the pressure sensor exceeds a predefined limit value:

reducing the water pressure in the drinking water line, in particular by deactivating or reducing the output of a water pump provided in the drinking water supply system, draining the water from the drinking water line at a flushing unit, or output of a user notification.

34. Drinking water supply system according to any one of embodiments 27 to 33, with the control device being configured to initiate control of the drinking water supply system according to a method according to embodiment 35.

35. Method for controlling a drinking water supply system according to any one of embodiments 1 to 34, comprising the following steps:

receiving measurement values, in particular measurement values for one or different properties of the water carried in the drinking water supply system, and controlling the drinking water supply system as a function of the received measurement values.

36. Computer program comprising commands the execution of which on at least one processor, in particular of a drinking water supply system according to any one of embodiments 1 to 34, initiates the performance of a method according to embodiment 35.

Further features and advantages of the present invention will become apparent from the following description of exemplary embodiments, with reference being made to the enclosed drawing.

BRIEF DESCRIPTION OF THE DRAWINGS

In the drawing,

FIGS. 1*a-b* show a section of a first exemplary embodiment of the drinking water supply system.

DETAILED DESCRIPTION OF THE PREFERRED EMBODIMENTS

Figure 1A:
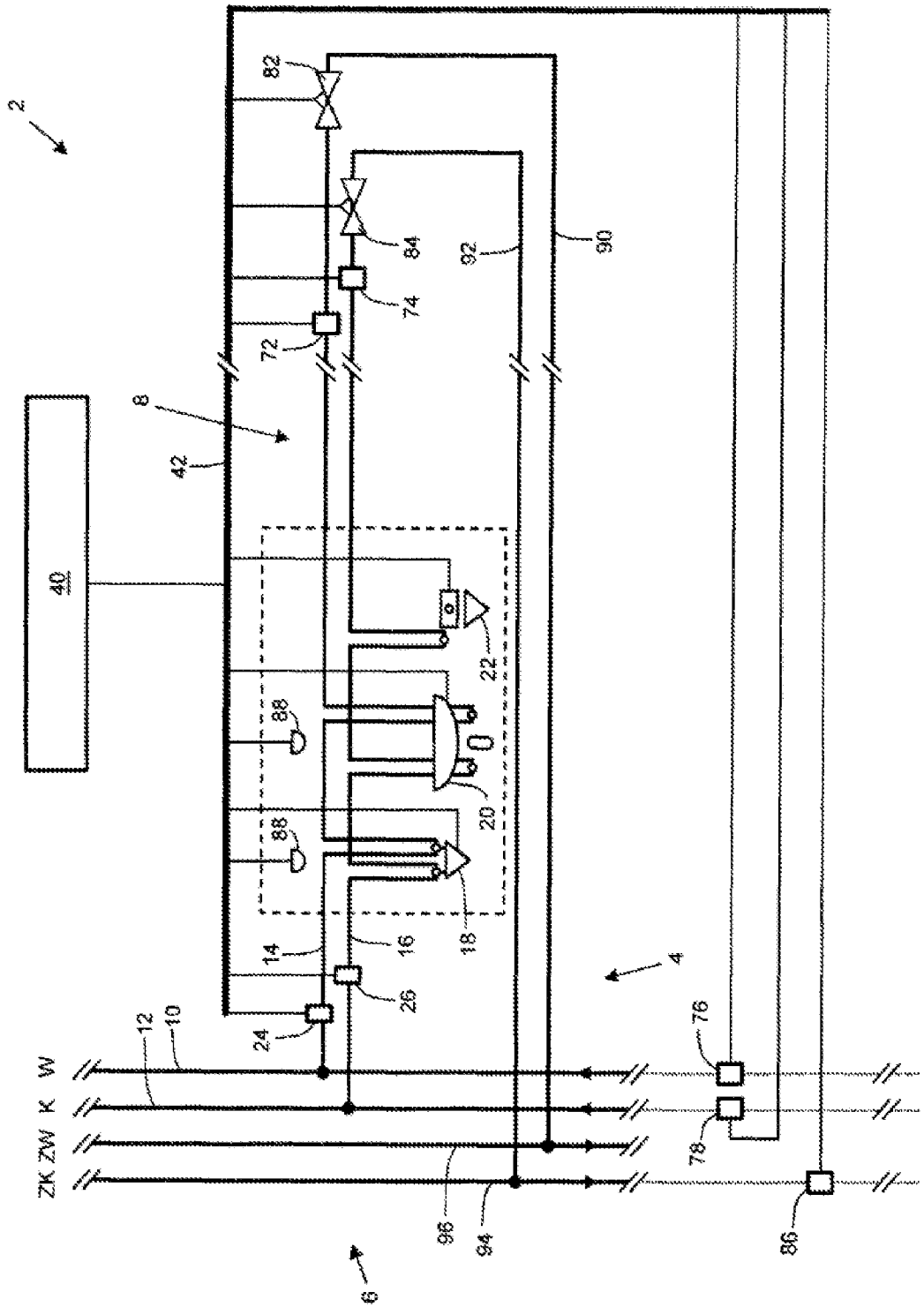

FIG. 1a shows a first exemplary embodiment of the drinking water supply system 2 in a schematic representation. FIG. 1b shows the section of the drinking water supply system 2, bordered in FIG. 1a with a dashed line, in enlarged representation.

The drinking water supply system 2 comprises a drinking water piping system 4 with a main supply line 6 and a plurality of subordinate supply lines, of which a subordinate supply line 8 is represented in FIG. 1. The main supply line 6 has a hot water supply line 10 ("W" in FIG. 1a) and a cold water supply line 12 ("K" in FIG. 1a) to which a respective hot water line 14 and cold water line 16 of the subordinate supply line 8 are connected.

Different drinking water tapping points are connected to the hot and cold water line 14, 16 of the subordinate supply line 8. FIG. 1 shows by way of example three drinking water tapping points of an individual wet cell with a first drinking water tapping point 18 as a shower mounting with hot and cold water connection, a second drinking water tapping point 20 as the wash basin mounting with cold and hot water connection and a third drinking water tapping point 22 as the WC flushing system with cold water connection. A plurality of further drinking water tapping points can be connected to the subordinate supply line 8, for example all wet cells of a hospital ward, a large shower or toilet system or also the drinking water tapping points of an operating theatre.

A plurality of further drinking water tapping points can be connected to the drinking water piping system 4. For example, the drinking water piping system 4 may be the drinking water piping system of a hospital with a plurality of structural sections or floors, with the individual floors, structural sections or wards of the hospital being supplied in each case by one or a plurality of subordinate supply lines which, in turn, are fed via the main supply line 6. If required, a plurality of main supply lines can also be provided which supply for example individual structural sections of the hospital.

For example, all wet cells of a hospital ward, a WC or shower block or also different drinking water tapping points of an operating theatre can be connected to a subordinate supply line 8.

As a whole, FIG. 1a therefore shows only a part of an entire drinking water supply system 2 which can have one or a plurality of main supply lines and a plurality of subordinate supply lines with a plurality of drinking water tapping points.

In the case of such a complex system with a plurality of pipelines and drinking water tapping points, there is the problem that a defect in the drinking water supply system, under certain circumstances, passes unnoticed or cannot be readily located. This can result in partial or complete failures of the drinking water supply and even contamination of germs of the drinking water. In particular, a lack of monitoring or maintenance of the drinking water supply system may lead to the desired drinking water quality not being continually achieved at the individual drinking water tapping points.

In order to overcome this problem, a plurality of sensors are provided in the drinking water supply system 2, which determine measurement values at different locations in the drinking water supply system 2, in particular for the water temperature, the water pressure, the water flow and/or for the drinking water quality of the water carried in the drinking water supply system 2.

FIG. 1a shows by way of example a first sensor 24 in the hot water line 14 of the subordinate supply line 8 and a sensor 26 in the cold water line 16 of the subordinate supply line 8. The sensors 24, 26 may for example be volume flow sensors which measure the water volume flowing through the respective pipeline per unit of time, they may be temperature sensors which measure the water temperature in the respective pipeline, or pressure sensors which measure the water pressure inside the respective pipeline. A plurality of these sensors can also be integrated into the drinking water lines 14, 16, for example in each case a volume flow sensor, a temperature sensor and/or a pressure sensor. Furthermore, corresponding sensors can also be provided at a plurality of positions of the drinking water lines 14, 16 in order to measure the water volume flowing through the pipelines, the water temperature and/or the water pressure at different positions of the drinking water lines 14, 16.

Sensors can also be integrated into the drinking water piping system 4 which determine measurement values for the drinking water quality, for example the pH value, the degree of hardness or the concentration of suspended solids or bacteria in the water. For example, the sensors 24, 26 may be corresponding sensors. Furthermore, such sensors can for example be provided in the cold water supply line 12 or the hot water supply line 10 of the main line 6 or directly behind the central feed point of the local water supplier into the drinking water supply system 2.

Furthermore, sensors are provided at the respective drinking water tapping points. For example, the shower mounting 18 for hot and cold water, as shown in FIG. 1b, is in each case equipped with a temperature sensor 28 and with a volume flow sensor 30 which measures the volume flow of the hot or cold water drained at the shower mounting 18. The wash basin mounting 20 also in each case has a temperature sensor 28 and a volume flow sensor 30 which measures the volume flow of the water drained at the wash basin mounting 20. Lastly, the WC flushing system 22 also has a temperature sensor 28 and a volume flow sensor 30 for the cold water drained at the WC flushing system.

In addition to the individual sensors, the drinking water supply system 2 has a central control device 40 which can receive and evaluate the measurement values recorded by the sensors. In order to transmit the measurement values from the sensors to the central control device 40, a field bus 42 is provided in the case of the exemplary embodiment shown in FIG. 1a-b, to which the individual sensors and the central control device 40 are connected. Alternatively to this, a star-shaped connection of the sensors to the central control device 40 can also be provided. Furthermore, wireless communication connections between individual sensors and the central control device are also conceivable, for example via radio, WLAN, Bluetooth or the like.

Figure 2:
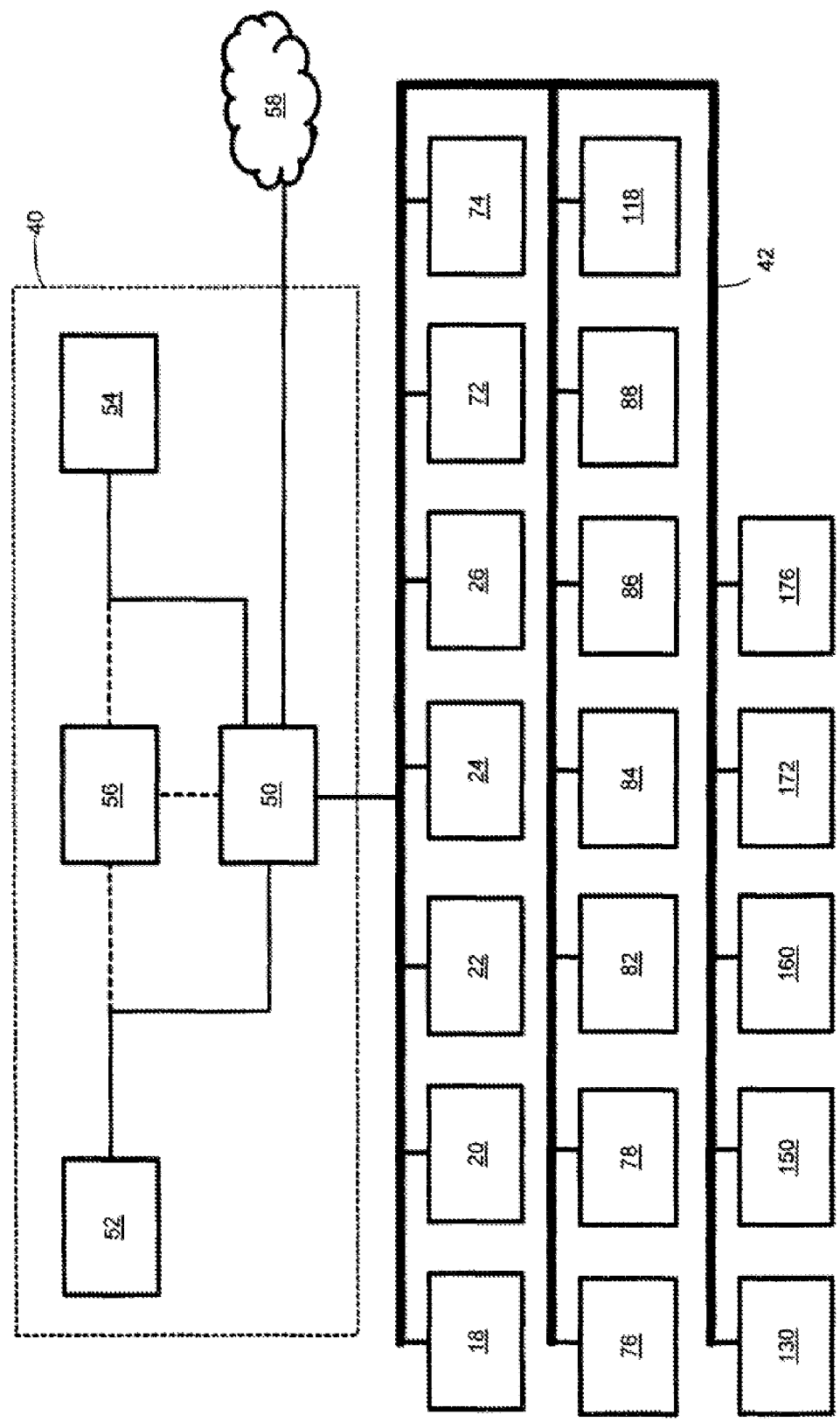
FIG. 2 shows an exemplary embodiment of the central control device of the drinking water supply system from FIG. 1*a*, FIG. 3a-d show four exemplary embodiments for cooling segments for the drinking water supply system from FIG. 1a, FIG. 4 shows a further section of the drinking water supply system from FIG. 1a, FIG. 5 shows a heat pump for the drinking water supply system from FIG. 1a, FIG. 6a-b show two exemplary embodiments for control elements for the drinking water supply system from FIG. 1a, FIG. 7 shows a further section of the drinking water supply system from FIG. 1a, FIG. 8 shows a further exemplary embodiment of the drinking water supply system.

FIG. 2 shows a possible structure of the central control device 40 from FIG. 1a. The central control device 40 comprises a controller 50 which can receive the measurement values of the sensors connected to the field bus via the field bus 42. The controller may for example be an electronic circuit with at least one programmable microcontroller.

Furthermore, the central control device 40 comprises one or a plurality of user interfaces 52 on which data received and/or evaluated by the controller 50 can be displayed. For example, the controller 50 can display the measurement values of the temperature sensors in a subordinate supply line 8 via the user interface 52 such that a user at the user interface 52 immediately obtains an overview of the water temperatures in the entire subordinate supply line.

In addition to the user interface 52, an electronic interface 54 is provided via which the data received or evaluated by the controller 50 can be transferred for further processing or storage to an external computer. In this manner, the measurement data is for example further evaluated or archived with the aid of the external computer.

The central control device 40 can also have a front end 56 which is supplied with data received and/or evaluated by the controller 50. Further evaluations can then take place in the front end 56 or user-controlled evaluations can be carried out. The entire evaluation can also be transferred to the front end 56 such that the measurement data received by the sensors has to be forwarded by the controller 50 only to the front end 56.

The front end 56 may for example be the front end of an existing building automation system, for example of a building ventilation or heating system. In this manner, a plurality of subsections of a building or a facility can be monitored and/or controlled from a central point. The front end 56 preferably has at least one microprocessor and a memory on which a computer program is stored with commands to illustrate and/or evaluate the measurement data transmitted by the sensors.

The front end 56 can, if required, also initiate outputs via the user interface 52 and via the interface 54, in particular when the measurement data is evaluated on the front end 56. The controller 50 or even the front end 56 can for example also be connected to a computer network or a cloud 58, for example in order to store measurement data or variables calculated therefrom or to retrieve control commands.

Providing the central control device 40 enables a central evaluation of the measurement values measured by the individual sensors, so that the state of the drinking water supply system 2 can be evaluated and optionally assessed at a central point.

Furthermore, it can be provided that the drinking water supply system 2 can be controlled by the central control device 40.

For this purpose, the drinking water supply system 2 comprises a plurality of decentralised control elements by means of which the water flow and the water temperature can be influenced at different points in the drinking water piping system 4.

In FIGS. 1a-b, the following control elements are shown by way of example and are explained below:
 a control element 70 on the WC flushing system 22,
 a respective actuatable separate flushing unit 72, 74 on the hot and cold water line 14, 16,
 a respective actuatable pump 76, 78 in the hot water supply line 10 and the cold water supply line 12 of the main supply line 6,
 a respective actuatable flow control valve 82, 84 on the respective end of the hot and cold water line 14, 16 and
 an actuatable cooling segment 86.

Providing the respective control elements and the central control device 40 for actuating these control elements makes it possible to control and optionally regulate the drinking water supply system 2 from a central point. For example, a user can actuate one or a plurality of the decentralised control elements from a central point by inputting a corresponding command via the user interface 52 or the front end 56.

The function of the individual control elements is explained below:

A flushing operation can be initiated with the control element 70 on the WC flushing system 22 so that water from the cold water line 16 is drained from the drinking water piping system 4. The control element 70 and the WC flushing system therefore constitute an actuatable flushing unit.

If a user determines for example on the basis of information output via the user interface 52 that the region of the cold water line 16 in which the WC flushing system 22 is located has not been flushed for a long time period and the water has been in the cold water line 16 for a long time, then he can initiate a flush via the central control device 40 and the control element 70 actuated thereby. As a result, a flushing operation is performed and water is drained from the corresponding piping section of the cold water line 16 such that fresh water can subsequently flow into the corresponding section of the cold water line 16. Similar control elements 70 can also be provided at other drinking water tapping points, for example at the shower mounting 18 or the wash basin mounting 20. In particular, a flush of the hot water line 14 can also be performed via the shower mounting 18 or the wash basin mounting 20.

The user can then for example also initiate such a flushing operation when he determines via the information displayed on the user interface 52 that the water temperature is too high in a certain piping section of the cold water line 16 or is too low in a certain piping section of the hot water line 14.

In the same manner, a flushing operation of the hot or cold water line can also be performed at a respective separate flushing unit 72, 74. Using such a flushing unit, water can be drained from the respective line independently of the drinking water tapping points. Such a flushing unit can for example have a pipeline outlet integrated into the respective line with an actuatable valve, such that by opening the valve water can be drained through the pipeline outlet from the line and for example channeled into an outflow provided therebelow.

The quantity of water carried in the respective drinking water line or the water pressure inside the respective drinking water line can also be influenced by a centrally initiated flushing operation at a drinking water tapping point or a flushing unit.

The drinking water supply system 2 further has presence detectors 88 in the form of motion sensors. The central control device 40 obtains information via the presence detectors 88 about whether a person is in the region of one of the drinking water tapping points 18, 20. The central control device is preferably configured to interrupt or prevent the performance of a centrally initiated flushing operation at one of the drinking water tapping points 18, 20 if the corresponding presence detector 88 detects the presence of a person. In this manner, a person in the region of the drinking water tapping points 18, 20 can be prevented from getting wet by being sprayed by an automatically initiated flushing operation, or from being scalded in the case of a hot water flushing operation.

Furthermore, a presence detector such as the presence detector 88 can also be used to automatically switch the control of the drinking water supply system 2 by the central control device 40 between a normal mode and an absence mode, for example a holiday mode. For this purpose, the control device 40 can be configured to automatically switch from a normal mode to an absence mode if no person has been detected for a predefined time period by the presence detector 88 or by further provided presence detectors. Furthermore, the control device 40 can be configured to automatically switch back to a normal mode if a person is detected by a presence detector during the absence mode. Different control programs can for example be stored for the normal mode and the absence mode in the central control device 40, which contain different commands to control the drinking water supply system 2 in the normal or absence mode.

The water pressure inside the hot and/or cold water supply line 10, 12 or the quantity of water flowing through the hot and/or cold water supply line 10, 12 can be influenced via the pumps 76, 78. If the user determines for example on the basis of the user interface 52 that the quantity of water or the water pressure available for the individual drinking water tapping points is too low, he can initiate an increase in the output of the pumps 76, 78 via the central control device 40.

Additionally or alternatively to the pumps 76, 78, pumps can also be provided in subordinate supply lines, for example in the subordinate supply line 8 in order to locally control the water flow or the pressure.

The hot water line 14 and the cold water line 16 are in each case connected via a flow control valve 82, 84 to a respective circulation line 90, 92 via which water can be circulated inside the drinking water piping system 4. In this manner, the water can be discharged from the hot water line 14 or the cold water line 16 without water having to be output from the drinking water supply system 2. The circulation lines 90, 92 are in the present exemplary embodiment connected to a corresponding central hot water circulation line 94 ("ZW" in FIG. 1*a*) and cold water circulation line 96 ("KW" in FIG. 1*a*) in the main supply line 6 via which the water inside the drinking water piping system 4 can be made available again for extraction. For example, the hot water circulation line 94 can channel the water to a unit in which it is heated before it is then fed back into the hot water supply line 10. The cold water circulation line 96 can for example channel the water to the actuatable cooling segment 86, in which the water is cooled before it is then fed back into the cold water supply line 12.

If a user for example determines via the user interface 52 that the water is in the hot water line 14 or the cold water line 16 for too long or is outside of the desired temperature range, he can discharge the water from the hot water line 14 or the cold water line 16 via the corresponding circulation line 90, 92 by actuating the corresponding flow control valve 82 or 84 such that fresh water subsequently flows in.

Since the circulation lines 90, 92 allow water to be discharged from the hot or cold water line 14, 16 without having to be drained from the drinking water supply system 2, water can be exchanged in the drinking water supply system without water being unnecessarily wasted. In particular, the water discharged through the circulation lines 90, 92 can be reused in the drinking water supply system 2.

Providing a circulation line is particularly advantageous in a cold water line since the water can be discharged in this manner when it has been heated above a predefined maximum temperature due to being in the cold water line for too long. The water can in this case be cooled down again to the desired temperature by the actuatable cooling segment 86.

Figure 3B:
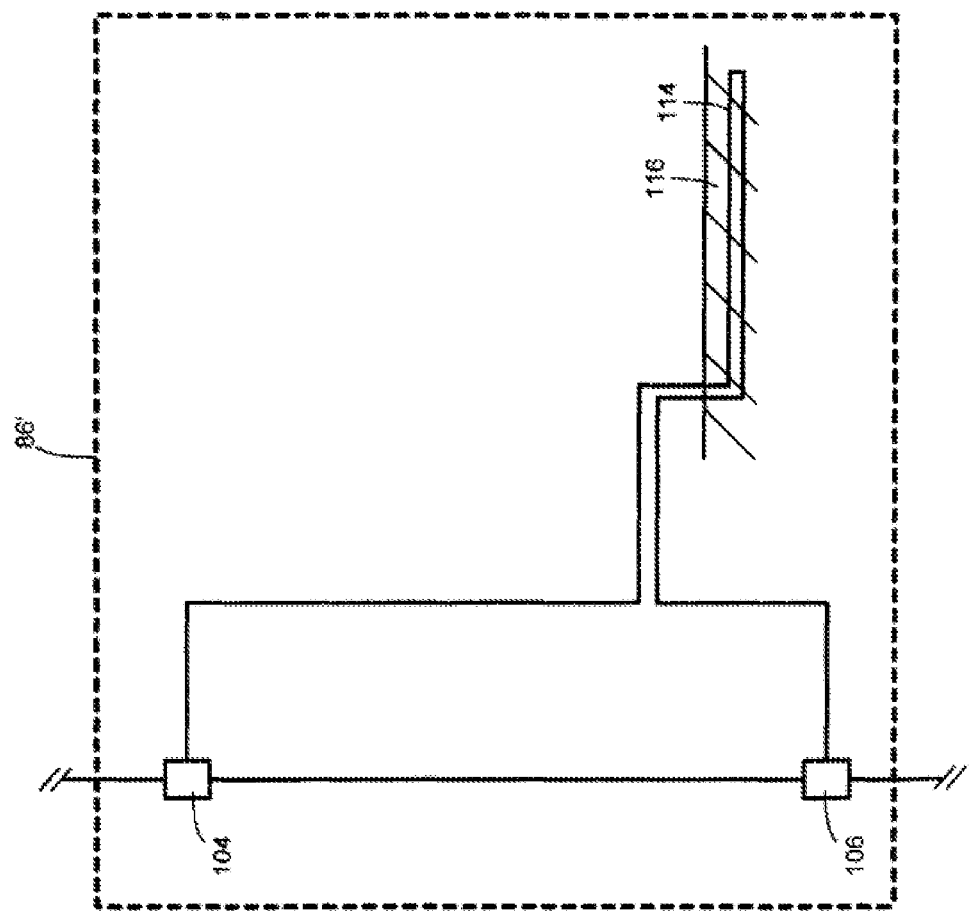
Figure 3A:
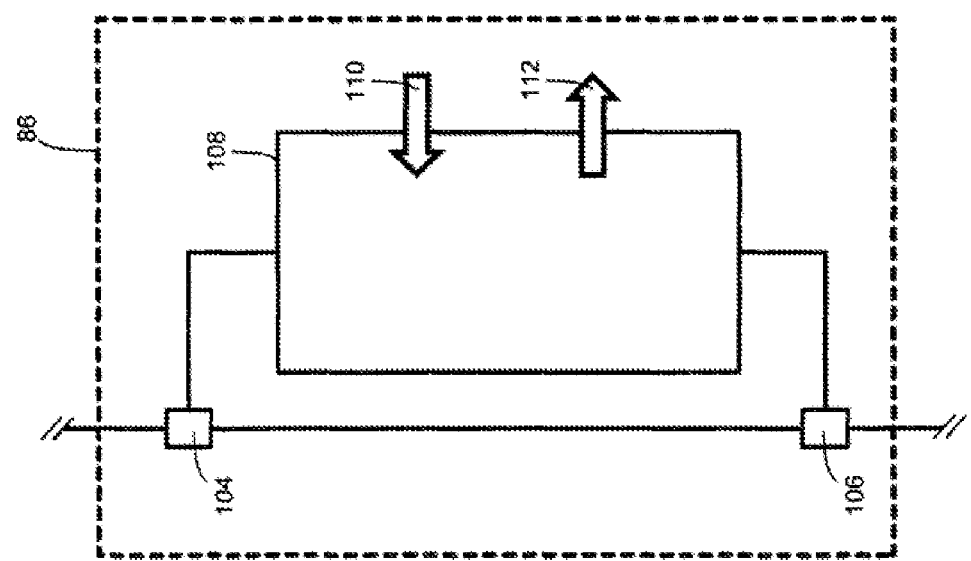

FIG. 3*a* shows a possible structure of the cooling segment 86. The cooling segment 86 is connected via two actuatable junction valves 104 and 106 to the cold water circulation line 94. The water flowing through the cold water circulation line 94 can be redirected into the cooling segment 86 by actuating the junction valves 104 and 106. A heat exchanger 108 is arranged in the cooling segment 86 with a coolant feed-in 110 and a coolant feed-out 112, by which the water flowing through the heat exchanger 108 can be cooled in order to achieve the desired water temperature for the cold water supply line 12.

FIG. 3*b* shows an alternative cooling segment 86'. The cooling segment 86' differs from the cooling segment 86 in that instead of an active cooling via a heat exchanger 108 operated with a coolant, a passive cooling takes place by virtue of the cooling segment 86' comprising a piping section 114 which is guided through a cold environment such as for example a cellar region or, as indicated in FIG. 3*b*, the soil 116.

Figure 3D:
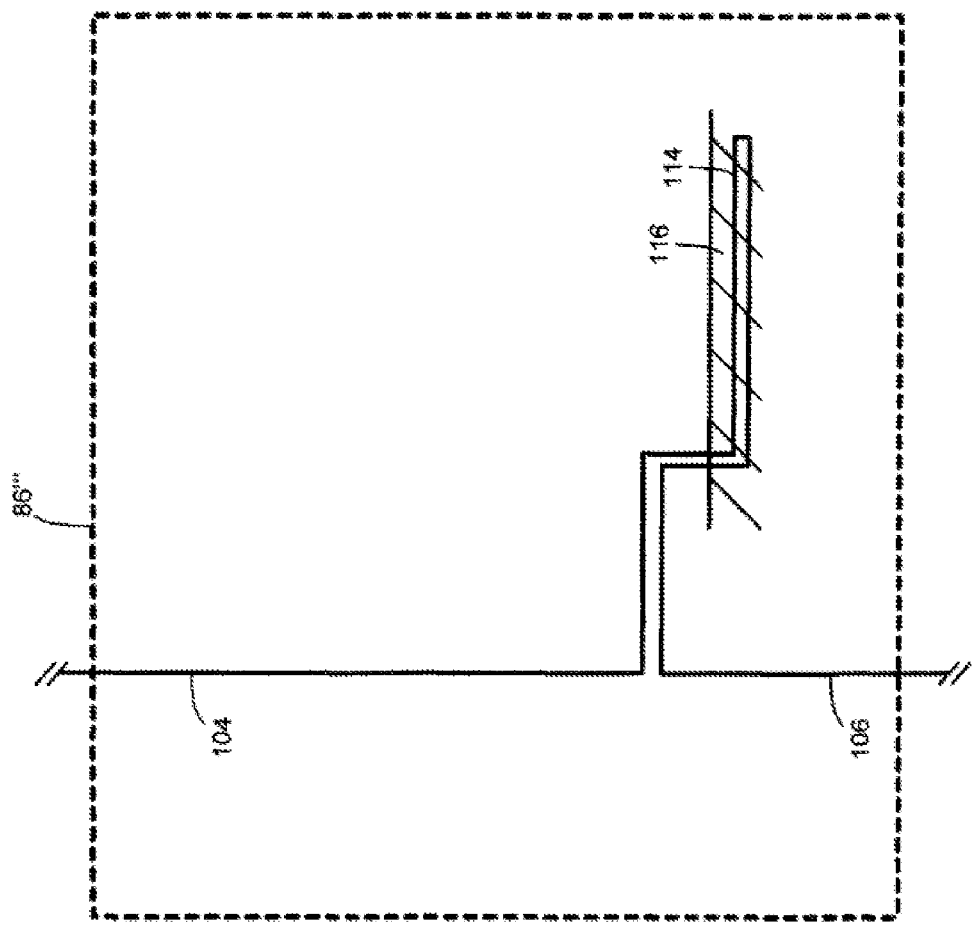
Figure 3C:
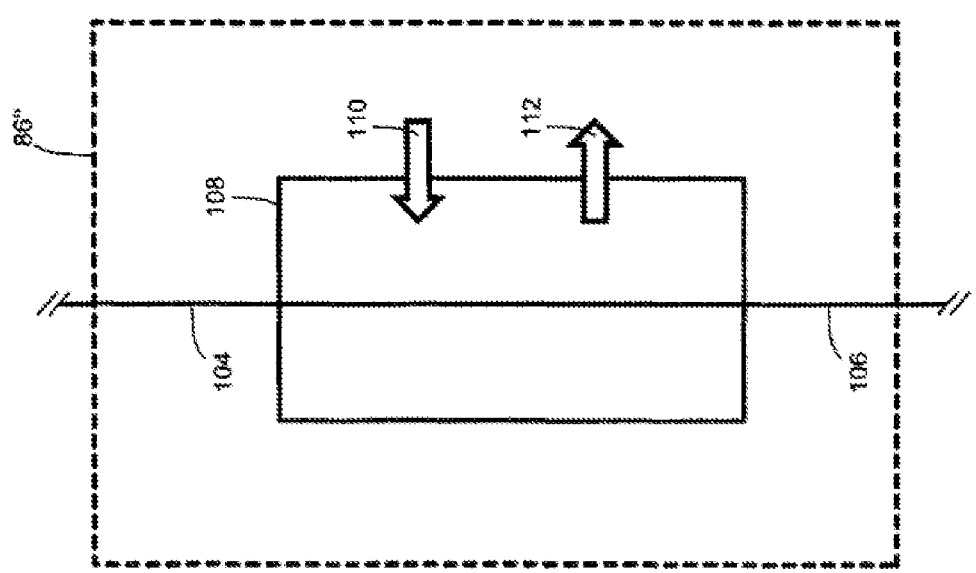

FIG. 3*c* shows a further alternative cooling segment. The cooling segment 86" has, like the cooling segment 86, a heat exchanger 108 with a coolant feed-in 110 and a coolant feed-out 112. Unlike the cooling segment 86, the heat exchanger 108 is, however, directly connected to the cold water circulation line 94. By activating or deactivating the coolant feed-in 110, the water flowing through the heat exchanger 108 can be cooled based on the time or requirements in order to achieve the desired water temperature for the cold water supply line 12. Alternatively, permanent cooling is also possible.

Like the heat exchanger 108, the piping region 114 of the cooling segment 86' can also be connected directly to the cold water circulation line 94; this is illustrated for the cooling segment 86''' in FIG. 3*d*.

Connecting the heat exchanger 108 or the piping region 114 directly to the cold water circulation line 94 has the advantage of avoiding dead water, as can arise in the case of the cooling segments 86 and 86' in the respectively unused piping section between the two junction valves 104 and 106.

Figure 4:
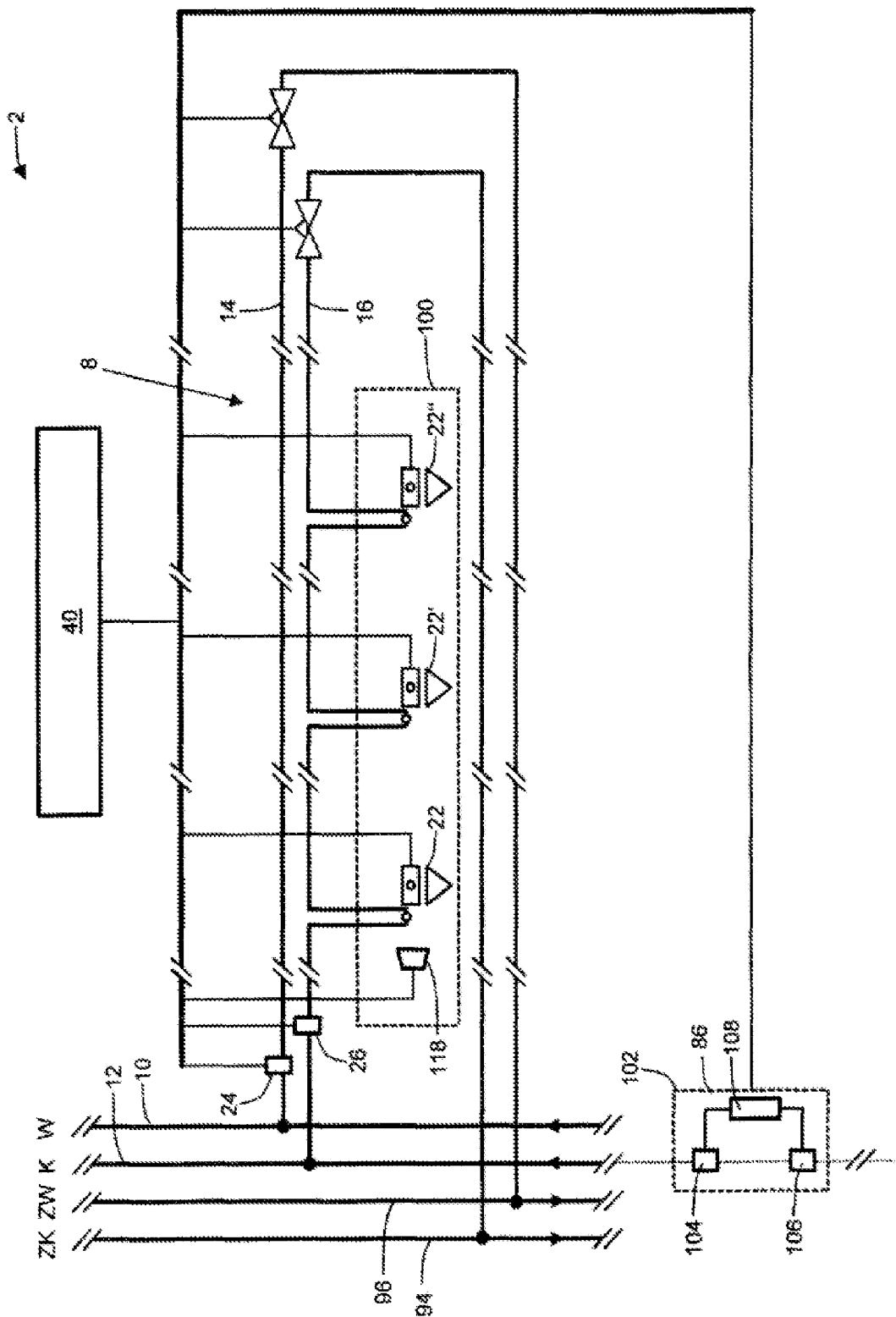

FIG. 4 shows a further section of the drinking water supply system 2 from FIG. 1*a*. For the sake of clarity, some components from FIG. 1*a* have been omitted in FIG. 4 and other components, which are not represented in FIG. 1*a*, have been portrayed. As FIG. 4 shows, not only can the drinking water tapping points 18, 20 and 22 shown in FIG. 1*a* be connected to the subordinate supply line 8, but rather further drinking water tapping points can also be connected, for example all drinking water tapping points of a hospital ward. Further WC flushing systems 22' and 22" are represented by way of example in FIG. 4 in addition to the WC flushing system 22. All WC flushing systems 22, 22' and 22" are, similar to the WC flushing system 22, provided with respective temperature sensors 28, volume flow sensors 30 and control elements 70 to initiate a flush.

The control device 40 enables a groupwise actuation of the control elements integrated into the drinking water supply system 2. All WC flushing systems 22, 22' and 22" of the subordinate supply line 8 are for example combined in FIG. 4 into a virtual group 100 and the control device 40 is configured to actuate the control elements 70 of the respective WC flushing systems together. For example, the controller 50 can be configured to receive via the user interface 52 a command to flush all WC flushing systems in the subordinate supply line 8 and, as a response thereto, to actuate the individual control elements 70 of the WC flushing systems from the group 100, such that a flushing operation is performed at all WC flushing systems of the group 100. A larger, preferably more turbulent volume flow is hereby achieved in the piping system, in particular in the subordinate supply line 8. The pipe walls can in particular be cleaned of impurities, such as for example a biofilm, by a turbulent volume flow.

Control elements of the cooling segment 86 can also be combined into a group. For example, the two actuatable junction valves 104 and 106 can be combined into a virtual group such that they are switched by a single command into a position in which the water is channeled through the cooling segment 86 or alternatively switched into a position in which the water is channeled past the cooling segment 86. Furthermore, the heat exchanger 108 can also be integrated into the virtual group such that for example a compressor and a pump for the coolant medium are started with the activation of the cooling segment 86 via the junction valves 104 and 106.

The central control device 40 can be further configured to determine by means of corresponding sensors at the WC flushing systems 22, 22', 22" in the subordinate supply line 8 whether the subordinate supply line 8 has been flushed at least once by a flush at one of the WC flushing systems 22, 22', 22" within a predefined time period and, if this is not the case, automatically cause a corresponding flush at some of the WC flushing systems 22, 22', 22". Such central monitoring of the flushing systems in the subordinate supply line 8 saves water compared to an autonomous and individual monitoring at each individual WC flushing system since flushing has to be performed less often and with less water.

A flushing operation initiated by the central control device 40, in particular at a plurality of WC flushing systems 22, 22', 22" at the same time, may lead to significant noise pollution. For this reason, the central control device 40 is preferably configured to perform the automatic flushing operations as a function of the time of the day. For this purpose, the controller 50 can for example have a system clock or be connected to such a system clock which provides a piece of information about the current time of the day. In this manner, automatic flushes in a hospital ward can for example be suppressed during the night. In an office building, flushes can also be performed in a specific manner at night when work is not in progress in the office building.

In order to further reduce noise pollution due to automatic flushing operations, the drinking water supply system 2 also has an acoustic sensor 118 in the form of a microphone which provides the central control device 40 with a measurement value for the volume level in a region to be monitored, for example in a hospital ward. The central control device 40 is preferably configured to automatically initiate flushing operations only if the volume level determined by the acoustic sensor 118 is below a predefined maximum volume level. Furthermore, the central control device 40 is configured to interrupt an automatically initiated flushing operation if said flushing operation causes the volume level to rise above a predefined maximum volume level. In this manner, a gain in convenience is achieved.

In the case of a further exemplary embodiment, the sensors 24, 26 can be configured to identify measurement values for the speed distribution of the water in the hot or cold water line. In this manner, it can be determined whether the water is flowing in a turbulent or laminar manner. If, for example in the case of a flush of the cold water line by an automatically initiated flush, it is determined at a plurality of the drinking water tapping points 22, 22', 22" that the water current in the cold water line 16 is laminar, the control device 40 can be configured to initiate further flushes in order to achieve higher flow speeds and as a result a turbulent current since a more reliable flush of the cold water line 16 can be effected by a turbulent current than by a laminar current, in particular in regards to the cleaning of the pipe wall. In the case of a laminar current, the current speed at the pipe wall approaches zero, while in the case of a turbulent current there, high current speeds occur due to the vortex.

FIG. 5 shows a heat pump 130 which is provided between the hot water supply line 10 and the cold water supply line 12 of the main supply line 6 of the drinking water supply system 2. The heat pump 130 comprises an evaporator 132 coupled to the cold water supply line 12, in which a heat transport medium evaporates, a compressor 134 to compress the evaporated heat transport medium, a condenser 136 coupled to the hot water supply line 10 to condense the compressed heat transport medium and an expansion valve 138 to expand the condensed heat transport medium. Through the energy expended to operate the compressor 134, a heat flow from the cold water supply line 12 to the hot water supply line 10 is achieved with the heat pump 130 such that the water in the cold water supply line 12 is cooled and the water in the hot water supply line 10 is heated. In this manner, simultaneous cooling of the cold water and heating of the hot water can be achieved in a resource-saving manner.

A heat pump corresponding to the heat pump 130 can for example also be provided between the hot and cold water line 14, 16 of the subordinate supply line 8.

Figure 6B:
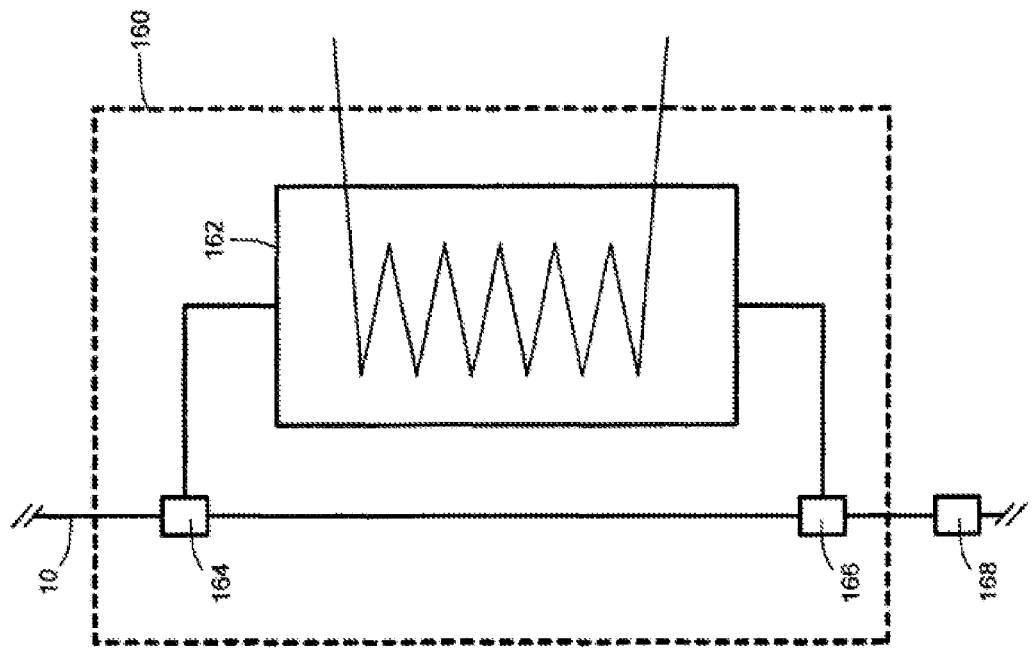
Figure 6A:
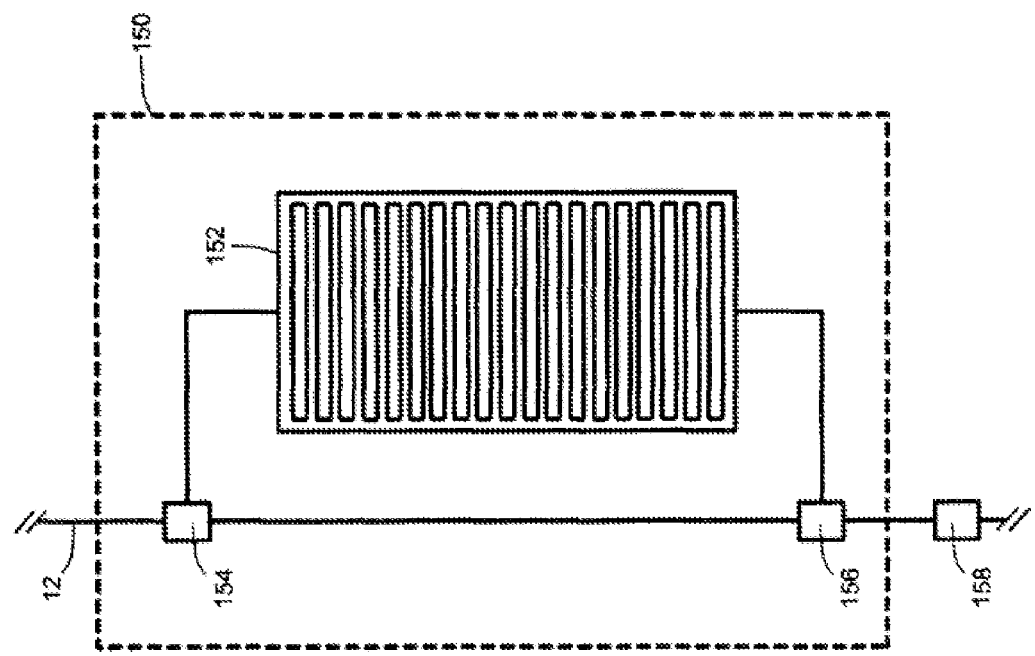

FIGS. 6a-b show two exemplary embodiments for further control elements of the drinking water supply system 2 from FIG. 1a. FIG. 6a shows an actuatable filter element 150 and FIG. 6b shows a sterilisation element 160. The filter element 150 or the sterilisation element 160 can for example be integrated into the cold water supply line 12 and/or into the hot water supply line 10. It is similarly possible to integrate a corresponding filter element or sterilisation element directly behind the central feed point of the local water supplier into the drinking water supply system 2.

The filter element 150 in FIG. 6a comprises a filter 152, for example a plate filter, and two actuatable junction valves 154, 156 by means of which the water can be channeled out of the cold water line 12 through the filter 152. Suspended solids or bacteria from the water can for example be filtered through the filter 152.

For the regulated actuation of the filter element 150, the drinking water supply system 2 can have a sensor 158 which measures the concentration of suspended solids or bacteria in the water channeled through the filter element 150. The central control device 40 can for example be configured to carry out an automatic actuation of the junction valves 154, 156 when the measured suspended solid or bacteria concentration exceeds a predefined maximum concentration such that the water is channeled through the filter 152.

The sterilisation element 160 in FIG. 6b comprises a sterilisation segment 162 and two actuatable valves 164, 166 by means of which the water can be channeled out of the hot water supply line 10 through the sterilisation segment 162. The water is sterilised in the sterilisation segment 162, for example by application of heat (as illustrated in FIG. 6b) or also by irradiation with intense UV light.

For the regulated actuation of the sterilisation element 160, the drinking water supply system can have a sensor 168 which measures the concentration of bacteria in the water channeled through the filter element 160. The central control device 40 can for example be configured to carry out an automatic actuation of the valves 164, 166 when the measured bacteria concentration exceeds a predefined maximum concentration such that the water is channeled through the sterilisation segment 162.

Figure 7:
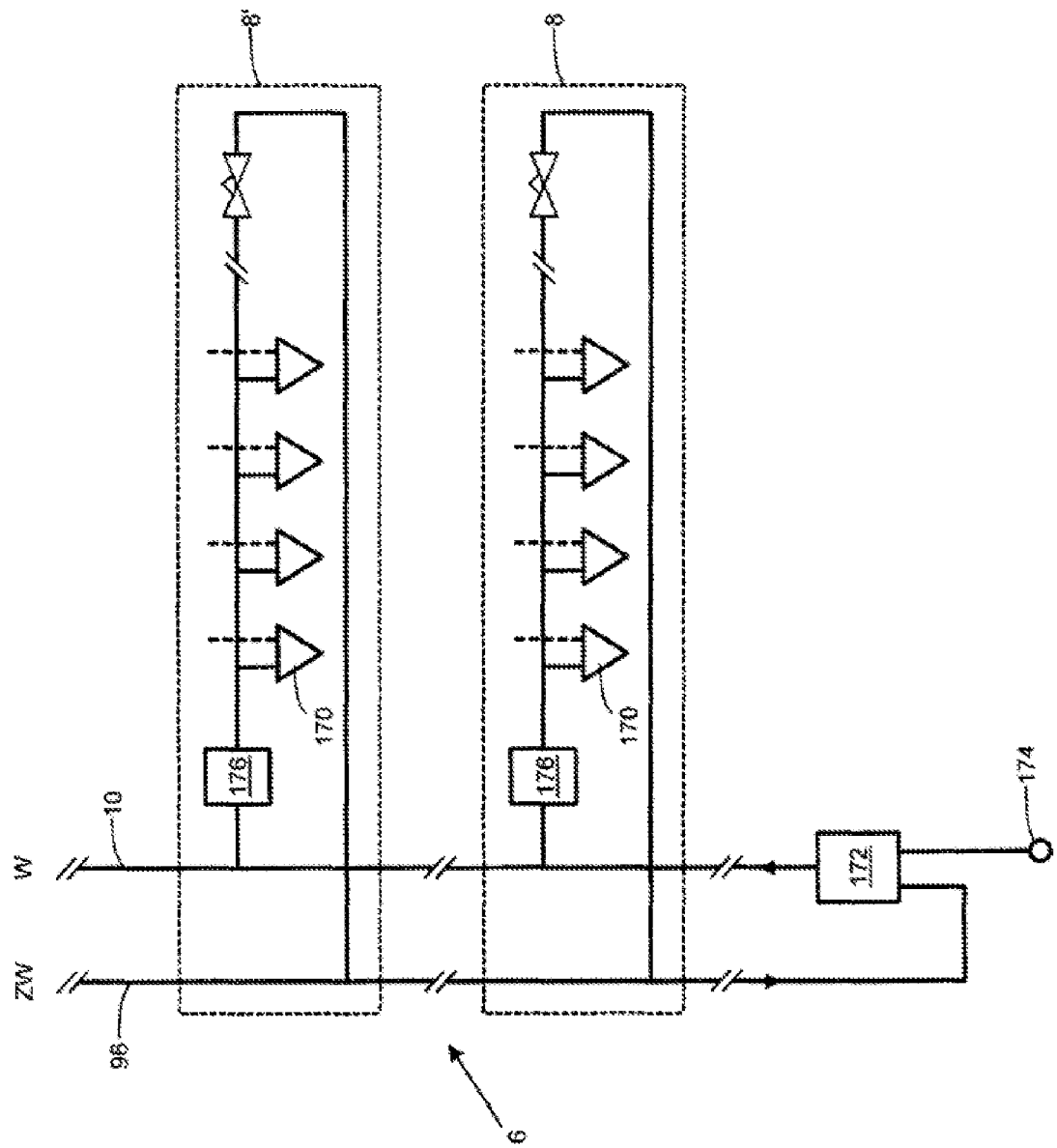

FIG. 7 shows a further section of the drinking water supply system 2 from FIG. 1a. For the sake of clarity, some components from FIG. 1a or 4 have been omitted in FIG. 7 and other components, which are not represented in FIG. 1a or 4, have been portrayed. FIG. 7 shows the hot water supply line 10 and the hot water circulation line 96 of the main supply line 6. The cold water supply line 12 and the cold water circulation line 94 are omitted in FIG. 7 for the sake of clarity.

A plurality of subordinate supply lines 8, 8' are connected to the main supply line 6 which are fed by the main supply line 6 and for example supply different floors of a larger building complex such as for example a hospital. A plurality of different drinking water tapping points 170 are integrated into the subordinate supply lines 8, 8', some of which are represented in FIG. 7.

A central hot water unit 172 is provided in the drinking water supply system 2 by means of which water made available, inter alia, by a central feed point 174 of the local water supplier can be heated to the desired water temperature for the hot water supply. Furthermore, the hot water circulation line 96 can also return the water circulated in the piping system to the hot water unit 172 in order to be reheated there.

The central hot water unit 172 is designed to heat water from room temperature to the desired temperature of for example 65° C. Furthermore, the throughput of the central hot water unit 172 is designed to supply the entire hot water portion of the drinking water supply system 2 and in particular all drinking water tapping points 170 integrated therein with hot water.

In the case of larger building complexes such as for example a hospital, partially large piping segments can be located between the central hot water unit 172 and the individual subordinate supply lines 8, 8'. In spite of pipeline insulation, the water can already be cooled down to such an extent that after quite a short time it has to be drained or transported via the hot water circulation line 96 back to the central hot water unit 172.

In order to enable a more economical operation of the drinking water piping system 2, decentralised hot water units 176 are integrated into individual subordinate supply lines 8, 8' by means of which the water in the hot water line of the respective subordinate supply line 8, 8' can be reheated to the desired temperature without having to be transported via the long hot water circulation line 96 back to the central hot water unit 172.

Since the water is already preheated by the central hot water unit 172, the decentralised hot water units 176 only have to be designed for a lower temperature difference, for example in order to heat water from 50° C. to 65° C. Furthermore, the throughput of the decentralised hot water units 176 only has to be adapted to the throughput of the respective subordinate supply line 8, 8'. In this manner, devices compactly dimensioned for the decentralised hot water units 176 can be used. In addition, a higher modularity and scalability of buildings is achieved. For example, individual decentralised hot water units can be put into or out of operation without influencing the entire system.

Figure 8:
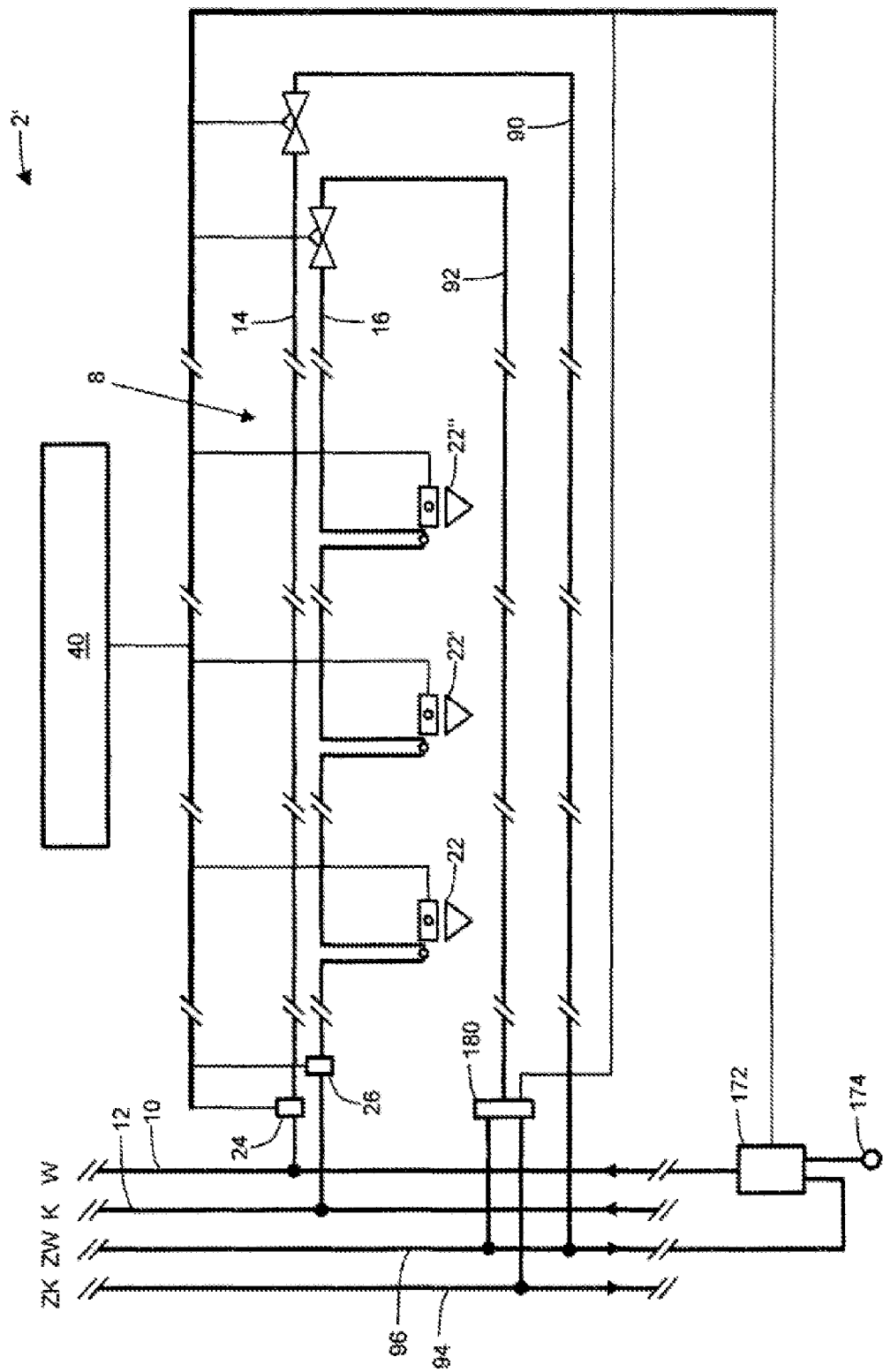

FIG. 8 shows a further exemplary embodiment of the system 2'. The structure and the functioning of the system 2' substantially correspond to the structure and the functioning of the system 2 such that reference is made to the description above. In particular, the same components are provided with the same reference signs.

In the system 2, the circulation line 92 for the cold water line 16 is connected to an actuatable three-way valve 180 such that the water can selectively be channeled from the circulation line 92 into the central cold water circulation line 94 or into the central hot water circulation line 96. The control device 40 is configured to actuate the three-way valve 180 such that water is channeled out of the circulation line 92 into the central hot water circulation line 94 when the water temperature measured using a temperature sensor for determining the water temperature in the cold water line 16, for example the sensor 26, or for determining the water temperature in the circulation line 92, exceeds a predefined limit value.

In this manner, water which could be contaminated by germs due to heating in the cold water line 16 can be reused inside the system 2' by being guided via the central hot water circulation line 94 to the hot water unit 172, in which it is heated, and as a result germs can be killed.

Instead of a three-way valve 180, it can also be provided that the water is essentially channeled from the circulation line 92 to the central hot water circulation line 94.

Different exemplary embodiments of the method for controlling the drinking water supply system 2 are described below on the basis of FIGS. 9 to 14. In particular, the control device 40 can be configured to control the drinking water supply system 2 according to the method. For this purpose, the controller 50 can for example have a memory on which a computer program is stored with commands the execution of which on at least one processor of the controller 50 initiates the performance of the respective method.

Figure 9:
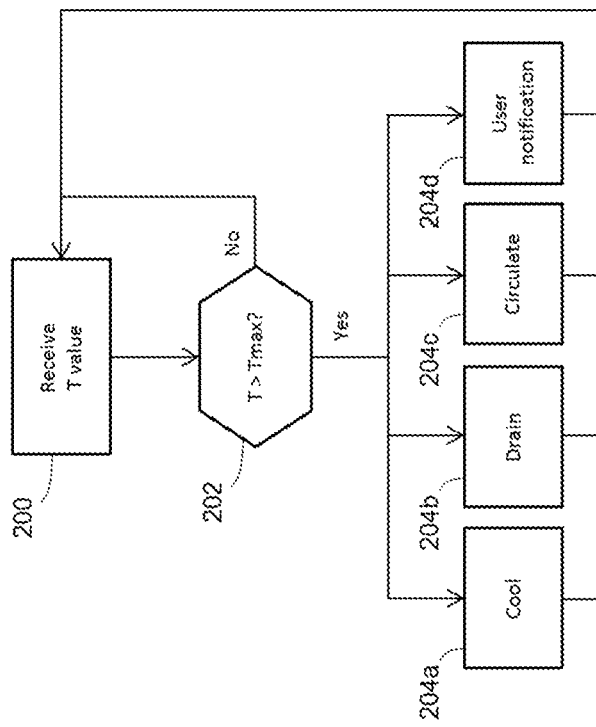
FIG. 9 shows an exemplary embodiment of the method for monitoring and regulating the cold water temperature.

FIG. 9 shows an exemplary embodiment of the method for monitoring and regulating the cold water temperature.

In the method, the central control device 40 receives, in the first step 200, temperature measurement values of temperature sensors 28, 26 from the cold water line, for example from the cold water line 16 of the subordinate supply line 8. In the second step 202, it is checked whether the measured temperature is above a predefined maximum temperature Tmax. As long as this is not the case, the process goes back to step 200. If the temperature exceeds the predefined maximum temperature Tmax, the central control device 40 causes the performance of one or a plurality of the steps 204a-d.

In step 204a, the drinking water from the cold water line 16 is cooled via the cooling segment 86. To this end, the control device 40 can for example actuate the control elements of the group 102, i.e. the junction valves 104, 106 and the heat exchanger 108 such that the water is channeled through the cooling segment 86 and is cooled there.

In step 204b, water is drained from the cold water line 16 by virtue of the control element 70 of a WC flushing system 22, 22', 22" or the separate flushing unit 74 being actuated.

In step 204c, the flow control valve 84 is actuated such that the water is discharged from the cold water line 16 of the subordinate supply line 8 via the circulation line 92, but remains inside the drinking water supply system 2.

In step 204d, the control device 40 causes the output of a user notification. For example, a person in charge of the safe operation of the drinking water supply system 2 can be informed of an increased risk of contamination of germs due to the excessively high cold water temperature.

Figure 10:
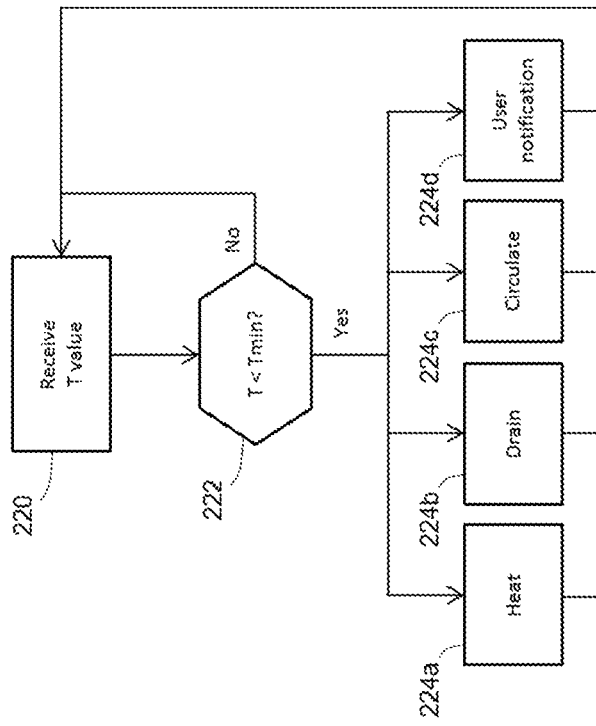
FIG. 10 shows a further exemplary embodiment of the method for monitoring and regulating the hot water temperature.

FIG. 10 shows an exemplary embodiment of the method for monitoring and regulating the hot water temperature.

In the method, the central control device 40 receives, in the first step 220, temperature values from sensors in a hot water line, for example from the sensor 24 or the temperature sensors 28 in the hot water line 14. In the second step 222, it is checked whether the temperature of the water in the hot water line has dropped below a predefined minimum temperature Tmin. If this is not the case, the process goes back to step 220. If the water temperature drops below the minimum temperature Tmin, the central control device 40 causes the performance of one or a plurality of the steps 224a-d.

In step 224a, a provided heating device, for example the decentralised hot water unit 176, is actuated in order to heat up the water from the hot water line.

In step 224b, the flushing unit 72 is actuated in order to drain water from the hot water line. In step 224c, the flow control valve 82 is actuated in order to discharge the water from the hot water line 14 via the circulation line 90. In this manner, the water in the piping section in question can be replaced before it is cooled further.

In step 224d, the control device 40 causes the output of a user notification, for example in order to indicate an increased risk of contamination of germs due to the excessively low hot water temperature.

Figure 11:
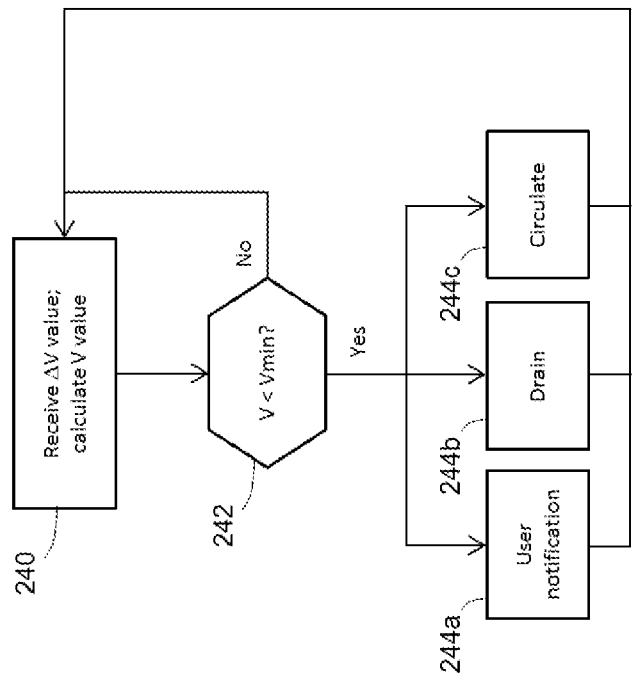
FIG. 11 shows a further exemplary embodiment of the method for monitoring and regulating the minimum throughput.

FIG. 11 shows an exemplary embodiment of the method for monitoring and regulating the minimum throughput through a drinking water line.

In the method, the central control device 40 receives, in a first step, the volume flow value from a volume flow sensor 24, 26, 30. The control device then calculates from the measurement values the volume of water flowing for a predefined time period through a certain piping section of a drinking water line.

In the second step 242, it is checked whether the calculated water volume value is below a minimum volume value Vmin. If this is not the case, the process goes back to step 240. Otherwise, the control device 40 causes the performance of one or a plurality of the steps 244a-c.

In step 244a, the control device 40 causes the output of a user notification. For example, an excessively low flow value through the drinking water line can indicate that a drinking water tapping point is defective and needs maintenance. The output of a user notification can then prompt a caretaker to perform a corresponding check.

In step 244b, the control device 40, by actuating the control elements 70 or the separate flushing unit 72 or 74, causes flushing and therefore draining of the water from the corresponding piping section of the drinking water line such that the volume flow in the corresponding drinking water line is increased by an artificially induced flush. In this manner, water is prevented from remaining for too long in the drinking water line and therefore contamination of germs of the water is prevented.

In step 244c, the control device 40, by actuating the flow control valves 82 and 84, causes water to be discharged from the drinking water lines 14, 16 via the circulation lines 90, 92 and therefore also artificially increases the volume flow.

Figure 12:
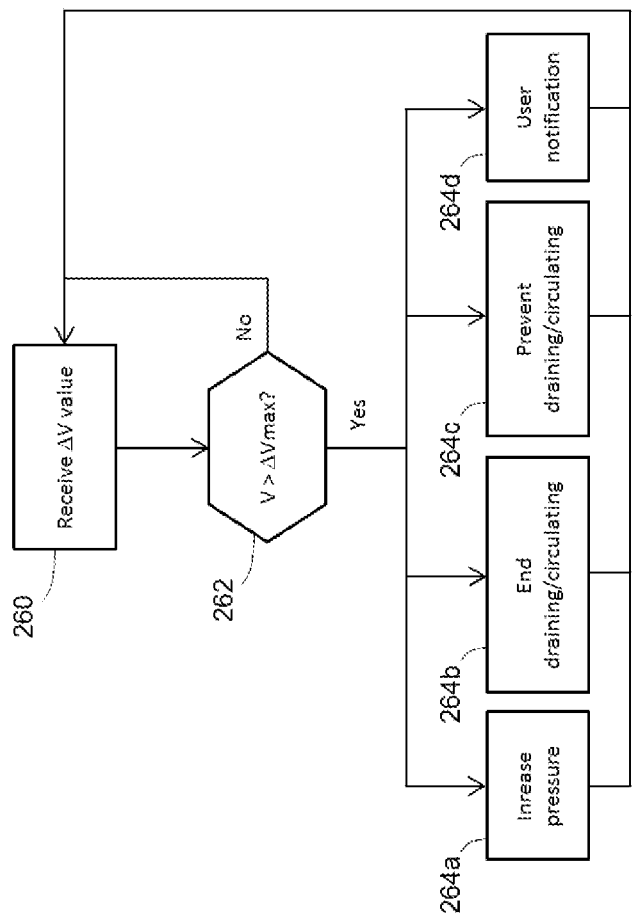
FIG. 12 shows a further exemplary embodiment of the method for monitoring and regulating as a function of usage.

FIG. 12 shows an exemplary embodiment of the method for monitoring and user dependent regulation. In the method, the central control device 40 receives, in a first step 260, measurement values for the volume flow, for example from the sensors 24, 26 and 30.

In step 262, it is checked whether the measured volume flow is above a maximum predefined volume flow ΔVmax. If this is not the case, the process goes back to step 260. If the maximally permissible volume flow is exceeded, this can indicate that the corresponding drinking water line is temporarily overloaded since water is being removed at too many points at the same time. As a countermeasure, the control device can then cause the performance of one or a plurality of the steps 264a-d.

In step 264a, the control device initiates a water pressure increase, for example by increasing the output of the pump 76 or 78 or by opening a provided supply line valve in order to provide more water or increased pressure for the drinking water line in question.

In step 264b, the control device causes the end of an operation which may be performed automatically, in which water is drained for example via the flushing unit 72, 74 or discharged via the circulation line 90, 92. In this manner, the otherwise automatically drained water is available for the other drinking water tapping points.

In step 264c, the control device 40 causes an automatic draining or circulating of the water to be prevented for a certain time period or while the permitted volume flow is exceeded. In this manner, the reliability of the supply is ensured at the individual drinking water tapping points.

In step 264d, the control device 40 causes the output of a user notification. For example, a person in charge can be informed of a possible supply bottleneck in the corresponding drinking water line.

Figure 13:
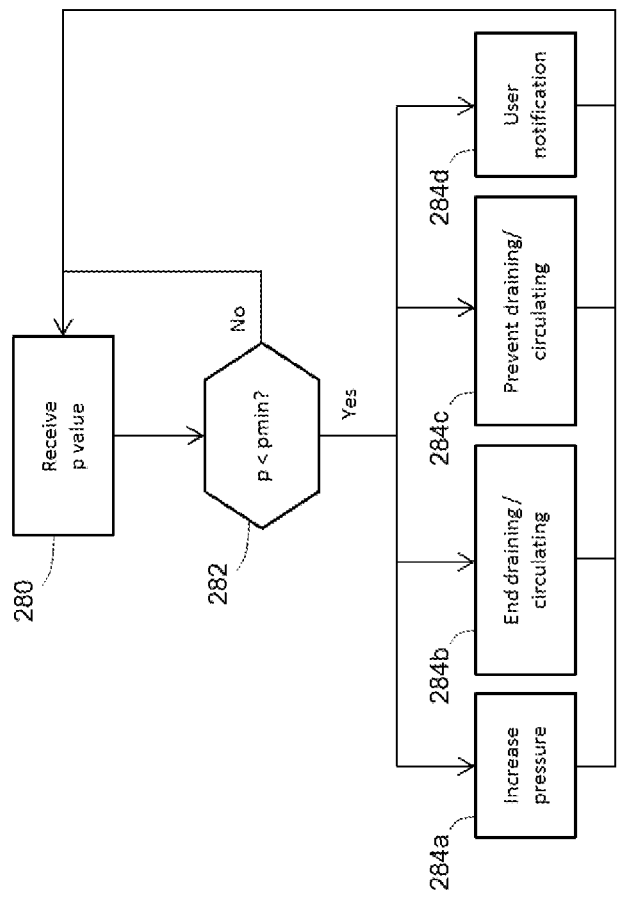

FIG. 13 shows an exemplary embodiment of the method for monitoring and regulating the pipeline pressure. In the method, the central control device 40 receives, in a first step 280, a measurement value for the water pressure in the drinking water line, for example from sensor 24 or 26.

In the second step 282, the control device 40 checks whether the measured pressure is below a minimum pressure pmin. If this is not the case, the process goes back to the first step 280. Otherwise, the control device causes the performance of one or a plurality of the steps 284a-d.

In step 284a, the control device 40 causes a water pressure increase, for example by increasing the output of the pumps 76 and 78 or by opening a supply line valve in order to increase the pressure in the pipelines.

In the steps 284b-c, any ongoing flushing or circulation operation is ended or future flushing or circulation operations are prevented.

In step 284d, the control device 40 causes the output of a user notification, for example to indicate the possibility of a leak which may also be the cause of a pressure drop. For example, the control device 40 can be configured to monitor the pressure inside a piping section for a longer time period and, in the case of an unusual pressure drop or a pressure drop which goes beyond normal fluctuations, it can be configured to indicate the risk of a possible leak.

Figure 14:
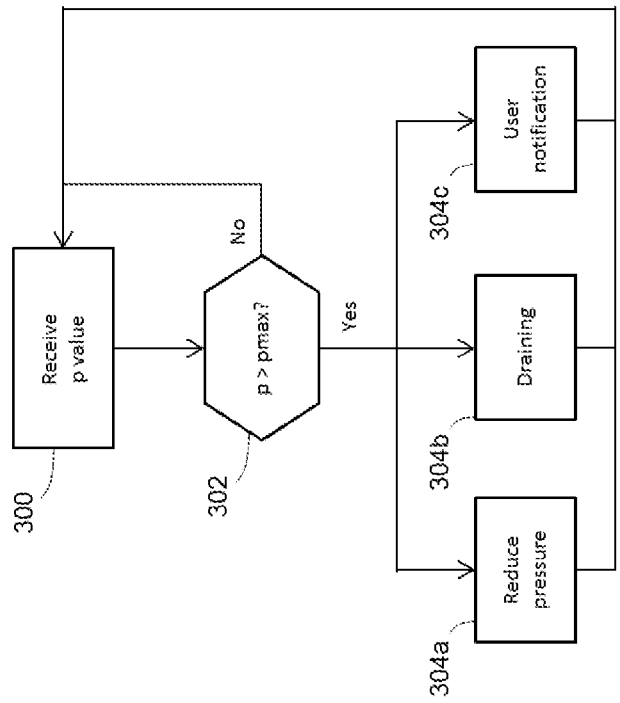
FIG. 13 shows a further exemplary embodiment of the method for monitoring and regulating the pipeline pressure and FIG. 14 shows a further exemplary embodiment of the method for monitoring and regulating the pipeline pressure.

FIG. 14 shows a further exemplary embodiment of the method for monitoring and regulating the pipeline pressure. In the method, the central control device 40 receives, in the first step 300, a value for the water pressure in the drinking water line in question, for example from the sensor 24 or 26.

In step 302, it is checked whether the measured pressure value is above a predefined maximum pressure pmax. If this is not the case, the process goes back to the first step 300. Otherwise, the control device initiates the performance of one or a plurality of the steps 304a-c.

In step 304a, the water pressure is reduced, for example by reducing the pump output of the pump 76 or 78 or by closing a supply line valve in order to reduce the pressure in the drinking water line in question. Alternatively or additionally, the control device 40 can also cause a valve to open, for example at a flushing unit.

In step 304b, for example by actuating the flushing unit 72 or 74, water is drained from the drinking water line in question in order to reduce the water pressure in the drinking water line in question.

In step 304c, the control device 40 causes the output of a user notification, for example in order to indicate a critical overpressure in the piping system.

Automatic pressure calibration can also be achieved by automatically monitoring and regulating the water pressure in the drinking water piping system 4 according to FIGS. 13 and 14. For example, a plurality of pressure sensors and a plurality of pumps and/or supply line valves can be provided on different floors of a building complex in which the drinking water piping system is installed. The water pressure on all floors can be regulated in a predefined pressure range by centrally monitoring the water pressure on the individual floors and automatically actuating the pumps and/or supply line valves as a function thereof.

Furthermore, a user-dependent pressure calibration can also be achieved hereby since the water pressure is automatically readjusted for example in the case of increased demand at a plurality of drinking water tapping points on one floor.

The invention claimed is:

1. A drinking water supply system comprising:
    a drinking water piping system,
    a plurality of drinking water tapping points connected to the drinking water piping system,
    at least one sensor configured to determine measurement values,
    a central control device configured to receive and evaluate the measurement values determined by the at least one sensor,
    a plurality of decentralised control elements configured to influence one or a plurality of properties of water carried in the drinking water supply system at different portions of the drinking water supply system, and
    a plurality of decentralised control devices, wherein each of the plurality of decentralised control devices are connected to one or more of the plurality of decentralised control elements for control thereof,
    wherein the central control device is configured to actuate the plurality of decentralised control elements to influence the one or the plurality of properties of the water carried in the drinking water supply system,
    wherein the central control device is configured to (i) receive a user input assigning at least two of the plurality of decentralised control elements to a virtual group, (ii) combine the at least two of the plurality of decentralised control elements to form the virtual group comprising the at least two of the plurality of decentralised control elements based on the received user input, and (iii) actuate the at least two of the plurality of decentralised control elements that form the virtual group when a virtual group actuation command is received to actuate the virtual group, and
    wherein the at least two of the plurality of decentralised control elements are connected to different decentralised control devices of the plurality of decentralised control devices.

2. The drinking water supply system according to claim 1, wherein the central control device is configured to actuate the at least two of the plurality of decentralised control elements of the virtual group, according to an actuation plan comprising the virtual group actuation command predefined for the at least two of the plurality of decentralised control elements that form the virtual group when the virtual group actuation command is received to actuate the virtual group.

3. The drinking water supply system according to claim 2, wherein the actuation plan contains a plurality of the virtual group actuation command for different control elements of the plurality of decentralised control elements, and the central control device is configured to actuate one or more of the plurality of decentralised control elements according to the actuation plan when the virtual group actuation command is received to carry out the actuation plan.

4. The drinking water supply system according to claim 1, wherein
    the drinking water piping system has a drinking water line,
    a group of the plurality of drinking water tapping points is provided which are connected to the drinking water line,
    a plurality of decentralised sensors is provided which are configured to determine information about a performance of flushing operations at drinking water tapping points of the group of the plurality of drinking water tapping points, and
    the central control device is configured to control the performance of flushing operations at individual drinking water tapping points of the group of the plurality of drinking water tapping points as a function of the information about the performance of the flushing operations at drinking water tapping points of the group of the plurality of drinking water tapping points.

5. The drinking water supply system according to claim 1, wherein
    one or a plurality of decentralised sensors are provided which are configured to determine information about a performance of flushing operations in a predefined section of the drinking water piping system, and
    the central control device is configured to monitor a time since a last flush in the predefined section of the drinking water piping system and to cause a flush in the predefined section of the drinking water piping system when a predefined maximum time is exceeded.

6. The drinking water supply system according to claim 1, wherein the central control device is configured to control the plurality of decentralised control elements as a function of the received measurement values.

7. A method for controlling the drinking water supply system according to claim 1, comprising:
    receiving the measurement values, in particular the measurement values for one or different properties of water carried in the drinking water supply system, and
    controlling the drinking water supply system as a function of the received measurement values,
    wherein the virtual group actuation command to actuate the virtual group is received and the at least two of the plurality of decentralised control elements of the virtual group are actuated, and wherein the at least two of the plurality of decentralised control elements are connected to different decentralised control devices of the plurality of decentralised control devices.

8. A non-transitory computer readable medium comprising instructions that when executed by at least one processor of a control device of the drinking water supply system cause the at least one processor to initiate a performance of the method according to claim 7.

9. The drinking water supply system of claim 1, wherein the plurality of decentralised control elements comprise flushing units that, when actuated, flush and/or drain water from the different portions of the drinking water supply system.

10. The drinking water supply system of claim 1, wherein the plurality of decentralised control elements comprise at least one of an actuable pump or an actuable flow control valve configured to influence water flow through the different portions of the drinking water supply system.

11. The method according to claim 7, wherein the virtual group actuation command to actuate the virtual group comprises a command to actuate the virtual group according to an actuation plan comprising actuation commands predefined for the at least two of the plurality of decentralised control elements that form the virtual group, wherein the at least two of the plurality of decentralised control elements that form the virtual group are actuated according to the actuation commands.

12. The method according to claim 7, further comprising initiating control of the drinking water supply system with the central control device.

13. The drinking water supply system according to claim 1, wherein the central control device is further configured to:
receive the measurement values, in particular the measurement values for one or different properties of water carried in the drinking water supply system, and
control the drinking water supply system as a function of the received measurement values,
wherein the virtual group actuation command for actuating the virtual group is received and the at least two of the plurality of decentralised control elements of the virtual group are actuated, and
wherein the at least two of the plurality of decentralised control elements are connected to different decentralised control devices of the plurality of decentralised control devices.

* * * * *